(12) United States Patent
Yu

(10) Patent No.: US 10,479,000 B2
(45) Date of Patent: Nov. 19, 2019

(54) METHOD FOR MANUFACTURING SAMPLE STORAGE DEVICE AND SAMPLE STORAGE DEVICE

(71) Applicant: Seung Kook Yu, Seoul (KR)

(72) Inventor: Seung Kook Yu, Seoul (KR)

(*) Notice: Subject to any disclaimer, the term of this patent is extended or adjusted under 35 U.S.C. 154(b) by 747 days.

(21) Appl. No.: 14/420,751

(22) PCT Filed: Jul. 19, 2013

(86) PCT No.: PCT/KR2013/006511
§ 371 (c)(1),
(2) Date: Feb. 10, 2015

(87) PCT Pub. No.: WO2014/025144
PCT Pub. Date: Feb. 13, 2014

(65) Prior Publication Data
US 2015/0202804 A1    Jul. 23, 2015

(30) Foreign Application Priority Data

Aug. 10, 2012 (KR) .................. 10-2012-0087681

(51) Int. Cl.
*B29C 35/08* (2006.01)
*B01L 3/00* (2006.01)
(Continued)

(52) U.S. Cl.
CPC .... *B29C 35/0805* (2013.01); *B01L 3/502707* (2013.01); *B29C 35/0888* (2013.01);
(Continued)

(58) Field of Classification Search
CPC ............... B29C 35/805; B29C 35/0888; B01L 3/502707
See application file for complete search history.

(56) References Cited

U.S. PATENT DOCUMENTS 3,482,733 A * 12/1969 Groves ................ B65B 69/00
                                                  206/820
6,143,576 A    11/2000 Buechler
(Continued)

FOREIGN PATENT DOCUMENTS

JP    2001156089 A    6/2001
JP    2004106320 A    4/2004
(Continued)

OTHER PUBLICATIONS

Microcavity Plasma Devices and Arrays Fabricated by Plastic-Based Replica Molding; Meng Lu, Sung-Jin Park, Brian T. Cunningham, and J. Gary Eden; Journal of Microelectromechanical Systems, vol. 16, No. 6, Dec. 2007; p. 1397-1402.*
(Continued)

*Primary Examiner* — Joseph S Del Sole
*Assistant Examiner* — John Robitaille
(74) *Attorney, Agent, or Firm* — Hauptman Ham, LLP

(57) ABSTRACT

According to the method for manufacturing a sample storage device and to the sample storage device of the present invention, a pattern forming mold having an engraved pattern part on the upper surface thereof is used to form a charging chamber sidewall on a first light-transmitting substrate, and a second light-transmitting substrate is adhered to the first light-transmitting substrate where the charging chamber sidewall is formed, and thus the sample storage device can be conveniently manufactured in large quantities.

2 Claims, 32 Drawing Sheets

(51) Int. Cl.
  *G01N 1/31* (2006.01)
  *B29L 31/00* (2006.01)
(52) U.S. Cl.
  CPC .................. *B01L 2300/0816* (2013.01); *B01L 2300/0819* (2013.01); *B01L 2300/0822* (2013.01); *B29C 2035/0827* (2013.01); *B29L 2031/752* (2013.01); *G01N 1/312* (2013.01)

(56) References Cited

U.S. PATENT DOCUMENTS

| | | |
|---|---|---|
| 2003/0180190 A1 | 9/2003 | Corcoran et al. |
| 2005/0272142 A1 | 12/2005 | Horita |
| 2007/0238164 A1 | 10/2007 | Kim |
| 2009/0073418 A1* | 3/2009 | Fukushima ............ G01N 1/312 356/39 |
| 2009/0302190 A1* | 12/2009 | Trieu ...................... B01L 3/565 248/683 |
| 2011/0241176 A1 | 10/2011 | Martin et al. |
| 2011/0243813 A1 | 10/2011 | Jackinsky et al. |

FOREIGN PATENT DOCUMENTS

| | | |
|---|---|---|
| JP | 2007240461 A | 9/2007 |
| JP | 2007253071 A | 10/2007 |
| JP | 2007279048 A | 10/2007 |
| JP | 2010243271 A | 10/2010 |
| KR | 100719238 B1 | 5/2007 |
| WO | 2008053693 A1 | 5/2008 |

OTHER PUBLICATIONS

International Search Report for PCT/KR2013/006511.
European Search Report dated Dec. 10, 2015 in connection with the counterpart European Patent Application No. 13828664.6.
Japanese Office Action dated Mar. 15, 2016 in connection with the counterpart Japanese Patent Application No. 2015-526460.

* cited by examiner

METHOD FOR MANUFACTURING SAMPLE STORAGE DEVICE AND SAMPLE STORAGE DEVICE

CROSS REFERENCE TO RELATED APPLICATION

This application claims the priority of Korean Patent Application No. 10-2012-0087681 filed on Aug. 10, 2012 in the Korean Patent and Trademark Office. Further, this application is the National Phase application of International Application No. PCT/KR2013/006511 filed on Jul. 19, 2013, which is incorporated herein by reference in its entirety.

TECHNICAL FIELD

The present disclosure relates to a method for manufacturing a sample storage device and the sample storage device, and more particularly, to a method for manufacturing a sample storage device, in which a sample storage device is manufactured by forming a charging chamber sidewall on one substrate through using a pattern forming mold having an engraved pattern part on the upper surface thereof and by adhering the other substrate to the substrate formed with the charging chamber sidewall, whereby it is possible to conveniently manufacture the sample storage device in large quantities, and the sample storage device manufactured thereby.

BACKGROUND ART

In general, when diagnosing a disease, the number and function of representative blood cells such as red blood cells, white blood cells or platelets contained in blood are scanned.

For example, tuberculosis, obesity or pregnancy may be diagnosed from an erythrocyte sedimentation rate, and dehydration or anemia may be diagnosed from a hematocrit.

Further, chronic leukemia may be diagnosed from the number of platelets. A kidney disease, hypoxia, smoking, lung disease, hemolytic anemia, aplastic anemia or the like may be diagnosed from the number of red blood cells. Acute appendicitis, leukemia or aplastic anemia may be diagnosed from the number of white blood cells.

In this way, the measurement of the number of cells such as blood cells are closely related with the diagnosis of a disease.

The sizes of red blood cells as representative blood cells are classified into four types of micro, normal, macro and mega. By identifying the size and number of red blood cells, they may be used as the material for the diagnosis of various diseases as described above.

In particular, scanning the number of red blood cells is essential to diagnose anemia and a cause thereof.

In the case of a general healthy person, approximately 4.4 to 5.6 million/dl red blood cells are contained in the blood in the case of a male, and 3.5 to 5 million/dl red blood cells are contained in the blood in the case of a female.

When it is found through the measurement of the number of red blood cells that the number of red blood cells is more than a reference value, diseases such as intrinsic plethora, dehydration, shock, renal failure or a cardiopulmonary disease may be diagnosed.

In addition, in the case of reduction in the number of red blood cells, various anemia may be diagnosed.

FIG. 1 is a perspective view illustrating an example of a conventional sample storage device for measuring the number of blood cells such as red blood cells.

As shown in FIG. 1, a conventional sample storage device 10 for measuring the number of red blood cells includes a body 15 which is generally formed of glass or quartz, a pair of partition walls 20 and 25 which are formed on the upper surface of the body 15, a measurement part 30 which is formed between the pair of partition walls 20 and 25, and a cover 35 which covers the measurement part 30 at an upward position.

The pair of partition walls 20 and 25 which are formed on the upper surface of the body 15 and the measurement part 30 which is positioned between the pair of partition walls 20 and 25 are formed by, for example, micromachining the body 15 which is formed of glass or quartz.

The pair of partition walls 20 and 25 are formed to project upward from the upper surface of the body 15 on both sides of the measurement part 30, and thus prevents a sample from leaking out of the measurement part 30 when dropping the sample such as blood into the measurement part 30.

The transparent cover 35 which is formed of glass is placed on the pair of partition walls 20 and 25, and the sample is positioned in the measurement part 30 between the pair of partition walls 20 and 25 and the cover 35 so that the number of cells, such as blood cells in blood, existing in the sample may be measured.

However, in the conventional sample storage device 10 as described above, since the body 15 and the cover 35 are separate from each other, a problem may be encountered in that the cover 35 should be positioned in place after dropping the sample into the measurement part 30.

Also, another problem may be encountered in that, in order to ensure adhesion between the cover 35 and the partition walls 20 and 25, it may be necessary to adhere the cover 35 to the partition walls 20 and 25 by separately using an adhesive or the like.

In order to cope with such problems, as shown in FIGS. 2 and 3, a sample storage device has been disclosed, in which an upper substrate 61 and a lower substrate 63 are adhered integrally with each other and a sample may be introduced through an inlet opening 61a defined in the upper substrate 61 and be charged in a flow path 61b such that the number of cells existing in the sample may be measured.

Nevertheless, in the conventional integral type sample storage device as described above, a problem may be caused in that, since the upper substrate 61 and the lower substrate 63 formed through injection molding should be stacked in a state in which they are aligned with each other by using an alignment jig and then should be adhered with each other by using an adhesive, a manufacturing procedure is complicated.

Moreover, because the upper substrate 61 and the lower substrate 63 are formed through injection molding to define a heightwise space (or protuberances) for forming a sample charging space, a problem may be caused in that substantial costs are incurred to fabricate molds for forming the respective substrates 61 and 63.

DISCLOSURE

Technical Problem

Various embodiments are directed to a method for manufacturing a sample storage device, in which a sample storage device is manufactured by forming a charging chamber sidewall on one substrate through using a pattern forming mold having an engraved pattern part on the upper surface thereof and by adhering the other substrate to the substrate formed with the charging chamber sidewall, whereby it is possible to conveniently manufacture the sample storage device in large quantities, and the sample storage device manufactured thereby.

Technical Solution

In an embodiment, a method for manufacturing a sample storage device having at least one charging chamber to count fine particles contained in a sample charged in the charging chamber may include: (a) preparing a pattern forming mold which has an engraved pattern part for forming at least a sidewall of the charging chamber, on an upper surface thereof; (b) pouring a predetermined amount of a liquid UV curable resin to be accommodated in the engraved pattern part, on the upper surface of the pattern forming mold; (c) seating a first light-transmitting substrate on the upper surface of the pattern forming mold and pressing them to each other; (d) radiating UV with the liquid UV curable resin accommodated in the engraved pattern part and thereby curing the liquid UV curable resin; (e) separating the first light-transmitting substrate which has the sidewall of the charging chamber formed as the liquid UV curable resin is cured, from the pattern forming mold; and (f) forming the charging chamber by adhering a second light-transmitting substrate to a surface of the first light-transmitting substrate on which the sidewall is formed.

In an embodiment, a method for manufacturing a sample storage device having at least one charging chamber to count fine particles contained in a sample charged in the charging chamber may include: (a) preparing a pattern forming mold which has an engraved pattern part for forming at least a sidewall of the charging chamber, on an upper surface thereof, the engraved pattern part being formed such that a plurality of pattern parts each of which forms a sidewall of a single charging chamber are arranged therein and thereby form sidewalls of a plurality of charging chambers; (b) pouring a predetermined amount of a liquid UV curable resin to be accommodated in the engraved pattern part, on the upper surface of the pattern forming mold; (c) seating a first light-transmitting base substrate on the upper surface of the pattern forming mold and pressing them to each other; (d) radiating UV with the liquid UV curable resin accommodated in the engraved pattern part and thereby curing the liquid UV curable resin; (e) separating the first light-transmitting base substrate which has the sidewalls of the plurality of charging chambers formed as the liquid UV curable resin is cured, from the pattern forming mold; (f) cutting the first light-transmitting base substrate such that the sidewalls of the plurality of charging chambers are divided into individual sidewalls of individual charging chambers and thereby defining first light-transmitting substrates; and (g) forming each charging chamber by adhering a second light-transmitting substrate to a surface of each first light-transmitting substrate on which the sidewall is formed.

In an embodiment, a method for manufacturing a sample storage device having at least one charging chamber to count fine particles contained in a sample charged in the charging chamber may include: (a) preparing a pattern forming mold which has an engraved pattern part for forming at least a sidewall of the charging chamber, on an upper surface thereof, the engraved pattern part being formed such that a plurality of pattern parts each of which forms a sidewall of a single charging chamber are arranged therein and thereby form sidewalls of a plurality of charging chambers; (b) pouring a predetermined amount of a liquid UV curable resin to be accommodated in the engraved pattern part, on the upper surface of the pattern forming mold; (c) seating a first light-transmitting base substrate on the upper surface of the pattern forming mold and pressing them to each other; (d) radiating UV with the liquid UV curable resin accommodated in the engraved pattern part and thereby curing the liquid UV curable resin; (e) separating the first light-transmitting base substrate which has the sidewalls of the plurality of charging chambers formed as the liquid UV curable resin is cured, from the pattern forming mold; (f) forming the plurality of charging chambers by adhering a second light-transmitting base substrate to a surface of the first light-transmitting base substrate on which the sidewalls of the plurality of charging chambers are formed; and (g) cutting the first and second light-transmitting base substrates which are adhered to each other such that the plurality of charging chambers are divided into individual charging chambers.

In the step (c), the pressing of the pattern forming mold and the first light-transmitting substrate to each other may be carried out as they pass through between a pair of pressing rollers, and the step (d) may be performed after the pattern forming mold and the first light-transmitting substrate pass through between the pair of pressing rollers.

The adhering of the pair of substrates may be performed by stacking them through applying a UV curable adhesive between them excluding a region corresponding to the charging chamber and then radiating UV.

The engraved pattern part may include a sidewall pattern for forming the sidewall of the charging chamber, and a plurality of line patterns which are spaced apart from one another by a predetermined interval at a region outside the sidewall pattern.

The engraved pattern part may include a grid pattern for forming grid scales, at a region inside the sidewall of the charging chamber.

The engraved pattern part may be constructed in such a manner that an electroformed mold which has a pattern for forming the sidewall of the charging chamber is fixed to the upper surface of the pattern forming mold.

The electroformed mold may be formed to include a grid pattern for forming grid scales, at a region inside the sidewall of the charging chamber.

The engraved pattern part may be constructed as a pattern for forming the sidewall of the charging chamber is etch-processed on the upper surface of the pattern forming mold base.

The etch-processed pattern forming mold may include a grid scale forming electroformed mold for forming grid scales, at a region inside the sidewall of the charging chamber.

A height of the sidewall may be set to approximately 10 μm to approximately 100 μm.

The pattern forming mold may use any one of a plate-shaped mold and a roll type mold on a circumferential surface of which a plurality of engraved pattern parts are formed.

In an embodiment, a method for manufacturing a sample storage device may include: preparing a first substrate; forming a pattern of a frame shape with prominences and depressions, on one surface of the first substrate; and forming a charging chamber inside the pattern, by adhering a second substrate to the pattern.

The pattern may be formed by curing a liquid UV curable resin.

A plurality of patterns may be formed, the first light-transmitting substrate may be cut such that the plurality of patterns are divided individually, and the second light-transmitting substrate may be adhered to each of the patterns.

A plurality of patterns may be formed, the second light-transmitting substrate may be adhered to the patterns, and the second light-transmitting substrate may be cut such that charging chambers are respectively formed by the plurality of patterns.

A pattern forming mold which is formed with an engraved pattern part may be prepared, a liquid UV curable resin may be filled in the engraved pattern part, and the pattern may be formed by curing the liquid UV curable resin.

The pattern forming mold may use any one of a plate-shaped mold and a roll type mold on a circumferential surface of which a plurality of engraved pattern parts are formed.

In an embodiment, a sample storage device manufactured by using the method for manufacturing a sample storage device may be provided.

Advantageous Effects

According to the embodiments, a sample storage device is manufactured by forming a charging chamber sidewall on one substrate through using a pattern forming mold having an engraved pattern part on the upper surface thereof and by adhering the other substrate to the substrate formed with the charging chamber sidewall. As a consequence, advantages are provided in that it is possible to conveniently manufacture the sample storage device.

Also, when manufacturing the sample storage device through the process described above, advantages are provided in that it is possible to manufacture the sample storage device in large quantities.

Moreover, when manufacturing the sample storage device through the process described above, advantages are provided in that it is possible to manufacture the sample storage device by using a flat plate-shaped substrate which does not necessarily require injection molding.

In addition, since the sidewall is formed by passing the pattern forming mold and the substrate through between a pair of pressing rollers and radiating UV to a liquid UV curable resin, advantages are provided in that a manufacturing time is shortened and mass production may be ensured.

Besides, by forming a plurality of line patterns in a region outside the pattern of the sidewall, since a UV curable adhesive for adhering a pair of substrates is filled and distributed in the spaces between the line patterns, it is possible to prevent the UV curable adhesive from leaking between the pair of substrates.

Further, by forming the engraved pattern part through fixing an electroformed mold to the upper surface of the pattern forming mold or etching the upper surface of the pattern forming mold, advantages are provided in that it is possible to finely control the thickness of the sidewall, the planar shape (print pattern) of the sidewall, and the print pattern width (print line width) of the sidewall.

Furthermore, since the pair of substrates are adhered by using the UV curable adhesive and UV, it is possible to adhere the pair of substrates within a short time.

MODE FOR INVENTION

Figure 1:
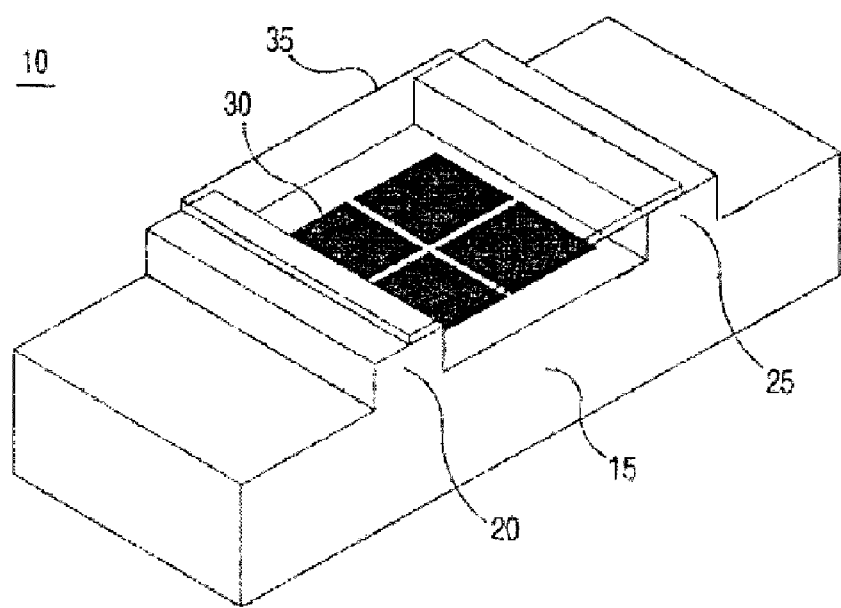
FIG. 1 is a perspective view illustrating an example of a conventional sample storage device.
Figure 2:
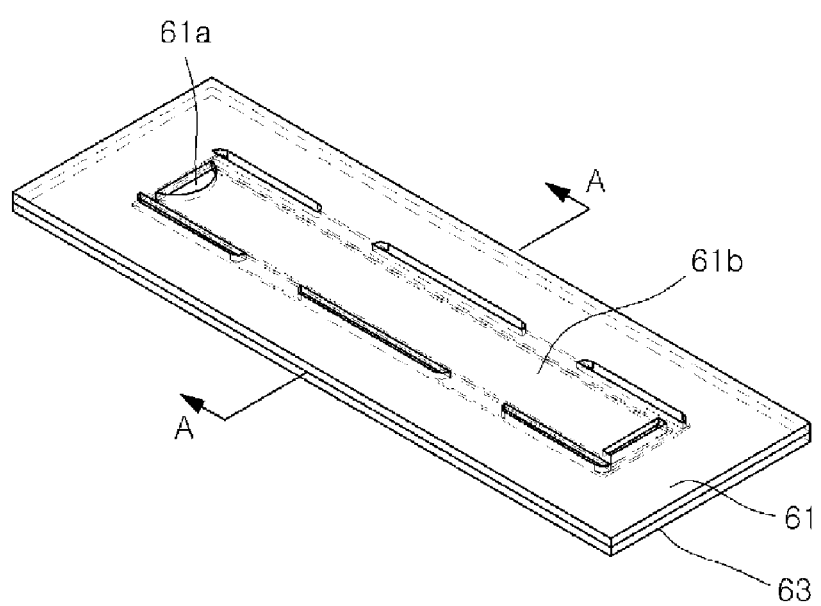
FIG. 2 is a perspective view illustrating another example of a conventional sample storage device.
Figure 3:
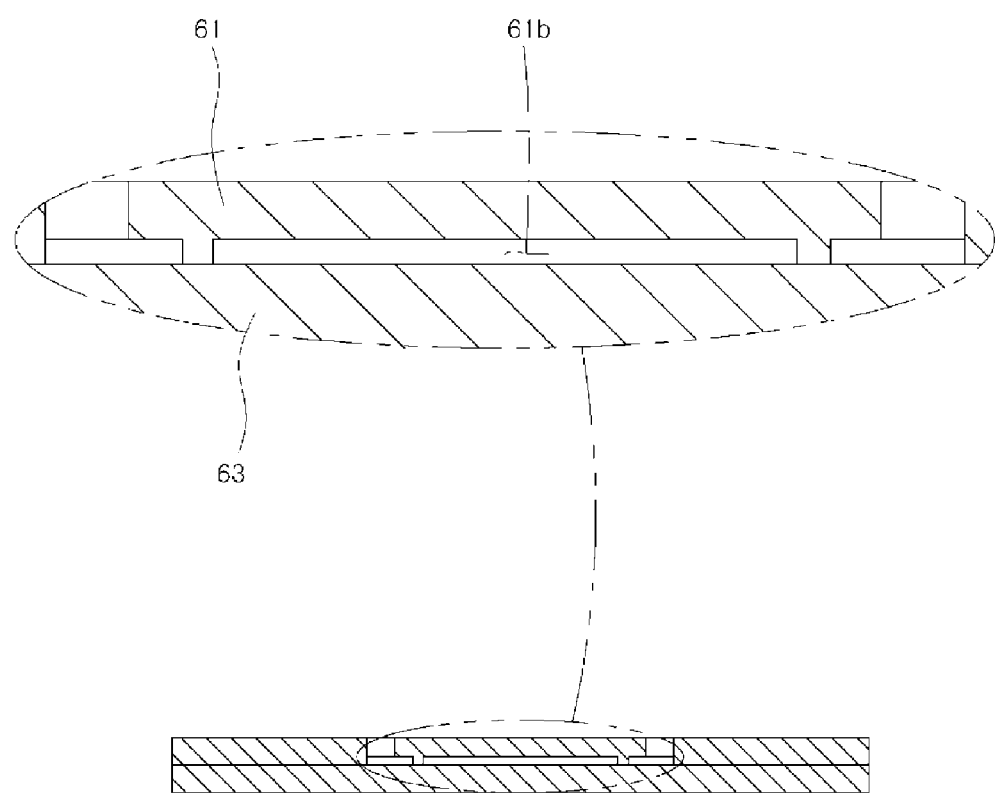
FIG. 3 is a cross-sectional view taken along the line A-A of FIG. 2.

The invention may be embodied in many different forms without departing form the technical spirit or features of the invention. Accordingly, the embodiments of the present invention are nothing but mere examples in all aspects and should not be construed as being limited to those set forth herein.

Also, even though terms like a first and a second may be used to describe various components in various embodiments of the present invention, the components or elements are not limited by these terms. These terms are used only to differentiate one component from another. Therefore, a component referred to as a first component in one embodiment may be referred to as a second component in another embodiment. As used herein, the term and/or includes any and all combinations of one or more of the associated listed items.

Also, when one component is referred to as being "connected/coupled" to another component, it should be understood that the former may be "directly connected" to the latter, or "indirectly connected" to the latter through at least one intervening component. In contrast, when a component is referred to as being "directly connected to" or "directly coupled to" another component, there are no intervening components present.

The terminology used herein is for the purpose of describing particular embodiments only and is not intended to limit the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by those skilled in the art to which the present invention pertains. It will be further understood that terms, such as those defined in commonly used dictionaries, should be interpreted as having meanings which are consistent with their meanings in the context of the relevant art and will not be interpreted in an idealized or overly formal sense unless expressly so defined herein.

Hereinafter, exemplary embodiments of the present invention will be described in detail with reference to the accompanying drawings. Like reference numerals in the drawings denote like elements, and thus their description will be omitted for conciseness. When it is determined that a specific description for the related known technology unnecessarily obscures the purpose of the invention, the detailed descriptions thereof will be omitted.

Figure 14:
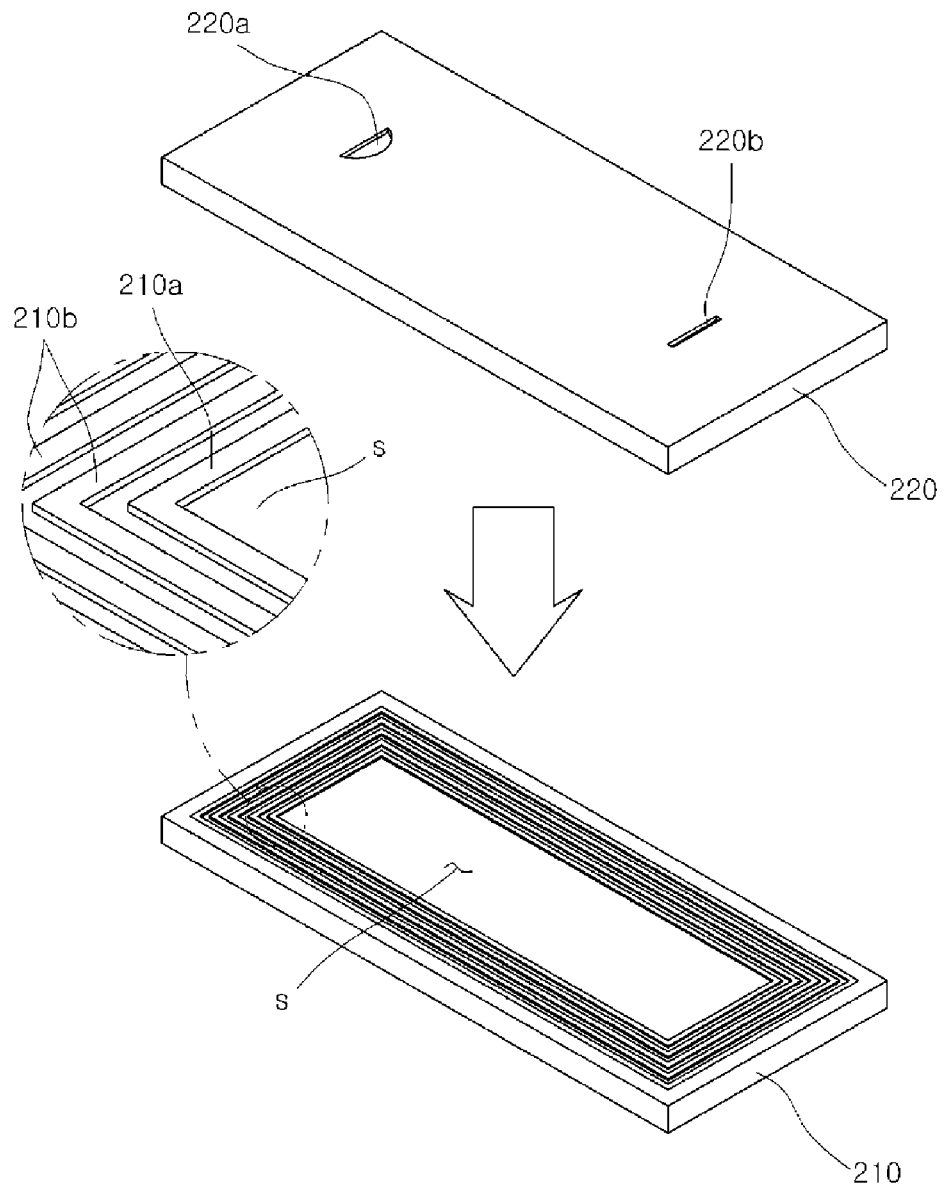
FIGS. 14 and 15 are perspective views illustrating the process of adhering the first light-transmitting substrate and a second light-transmitting substrate in accordance with the first embodiment.
Figure 15:
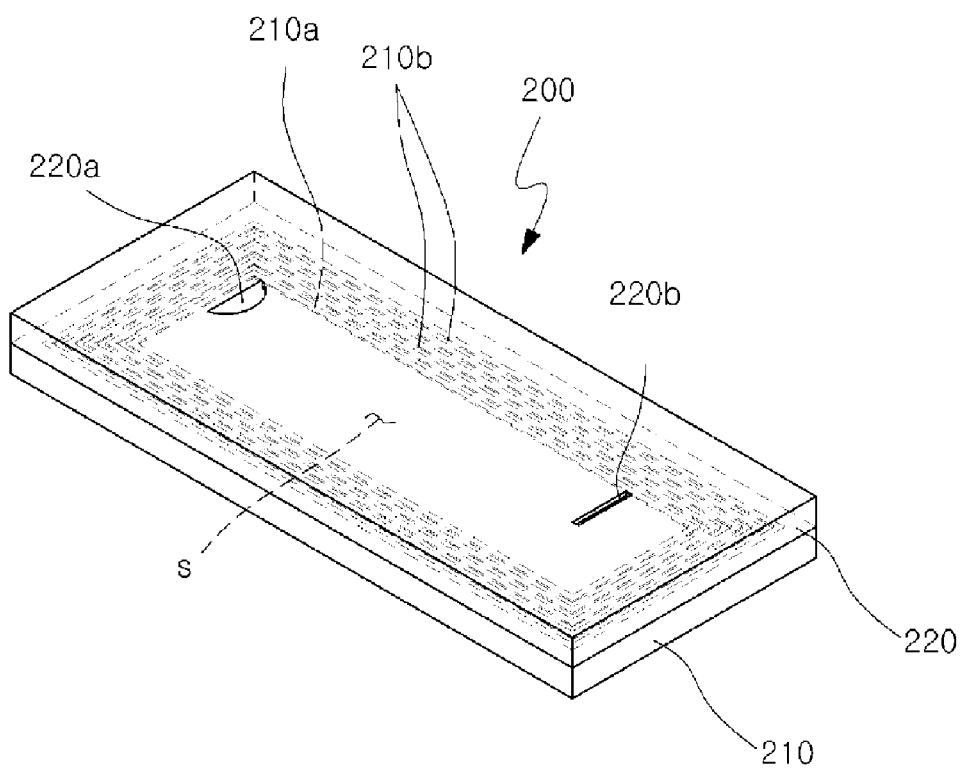

As shown in FIGS. 14 and 15, a sample storage device 200 in accordance with an embodiment is a device which includes at least one charging chamber s to count the number of the fine particles contained in a sample charged in the charging chamber s.

The sample storage device 200 is constructed to include a first light-transmitting substrate 210, a second light-transmitting substrate 220, a sidewall 210a, and line walls 210b.

The first light-transmitting substrate 210 forms one inner surface of the charging chamber s.

The second light-transmitting substrate 220 forms the other inner surface of the charging chamber s.

Each of the first light-transmitting substrate 210 and the second light-transmitting substrate 220 may be formed of any one material among polycarbonate, poly methyl methacrylate, polyethylene, polyethylene terephthalate, polystyrol and glass. The sidewall 210a is formed to a predetermined height between the first light-transmitting substrate 210 and the second light-transmitting substrate 220, and constructs the sidewall of the charging chamber s. The sidewall 210a is formed by curing a liquid UV (ultraviolet) curable resin RS.

As described above, the charging chamber s is formed by the first light-transmitting substrate 210, the second light-transmitting substrate 220 and the sidewall 210a.

A plurality of line walls 210b are formed at regular intervals outside the sidewall 210a. An adhesive for adhering the first light-transmitting substrate 210 and the second light-transmitting substrate 220 may be applied between the line walls 210b.

The sidewall 210a of the charging chamber s is formed to have a height of approximately 10 μm to 100 μm.

Meanwhile, an introducing part 220a for charging a sample into the charging chamber s and a discharging part 220b for discharging the sample or air are formed in any one substrate of the first light-transmitting substrate 210 and the second light-transmitting substrate 220. For example, as shown in FIGS. 14 and 15, the introducing part 220a and the discharging part 220b may be formed in the second light-transmitting substrate 220.

Hereafter, methods for manufacturing the sample storage device 200 as described above will be described in detail.

FIRST EMBODIMENT

Figure 4:
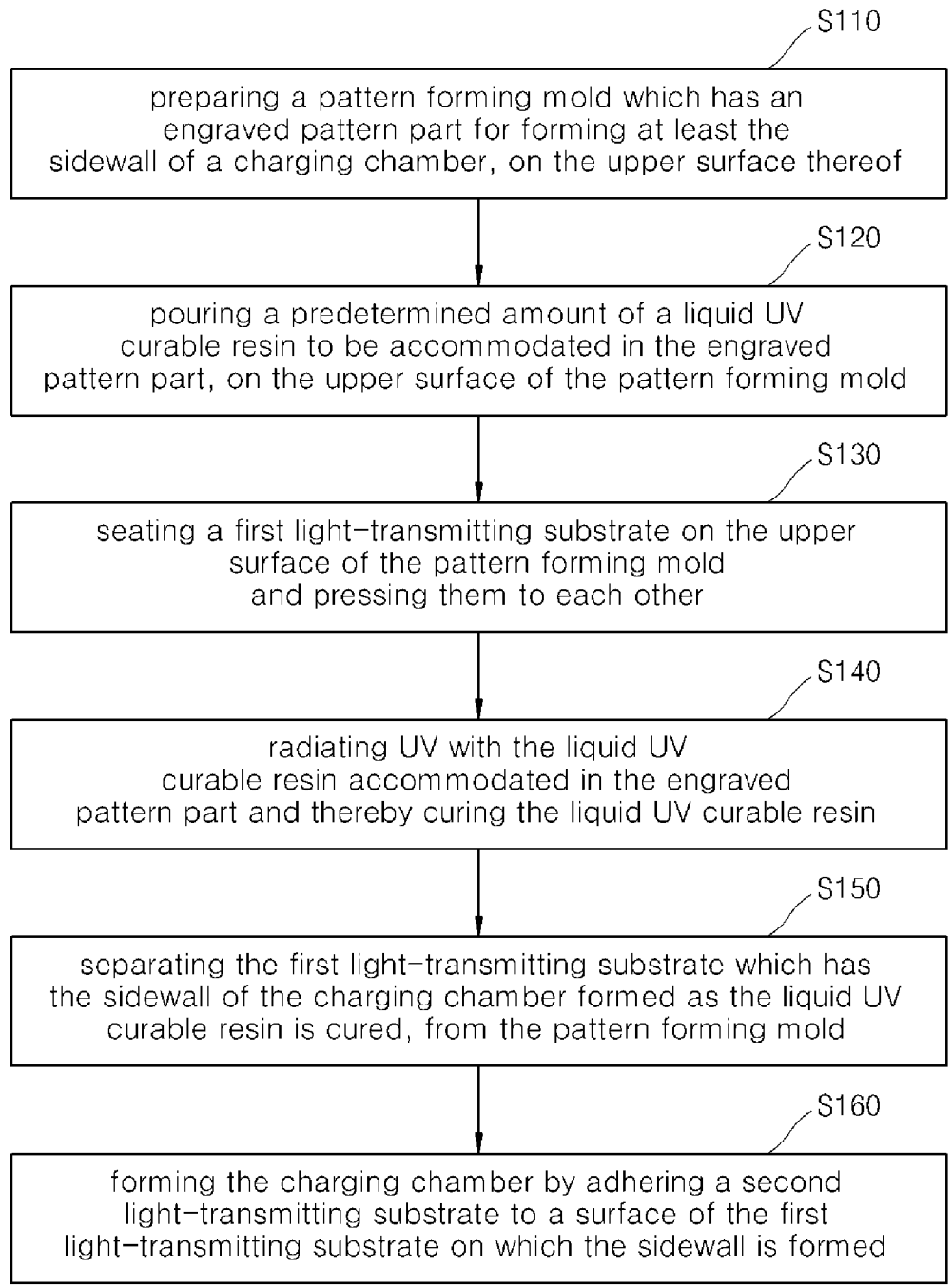
FIG. 4 is a flow chart explaining a method for manufacturing a sample storage device in accordance with a first embodiment.

As shown in FIG. 4, a method for manufacturing a sample storage device in accordance with a first embodiment includes (a) preparing a pattern forming mold which has an engraved pattern part for forming at least the sidewall of a charging chamber, on the upper surface thereof; (b) pouring a predetermined amount of a liquid UV curable resin to be accommodated in the engraved pattern part, on the upper surface of the pattern forming mold; (c) seating a first light-transmitting substrate on the upper surface of the pattern forming mold and pressing them to each other; (d) radiating UV with the liquid UV curable resin accommodated in the engraved pattern part and thereby curing the liquid UV curable resin; (e) separating the first light-transmitting substrate which has the sidewall of the charging chamber formed as the liquid UV curable resin is cured, from the pattern forming mold; and (f) forming the charging chamber by adhering a second light-transmitting substrate to a surface of the first light-transmitting substrate on which the sidewall is formed.

First, the step (a) will be described.

The step (a) is the step of preparing a pattern forming mold 100 which has an engraved pattern part 104 for forming at least the sidewall 210a of the charging chamber s, on the upper surface thereof.

The engraved pattern part 104 may be formed into various patterns to form various shapes which include the sidewall 210a of the charging chamber s, outside the charging chamber s.

Figure 8:
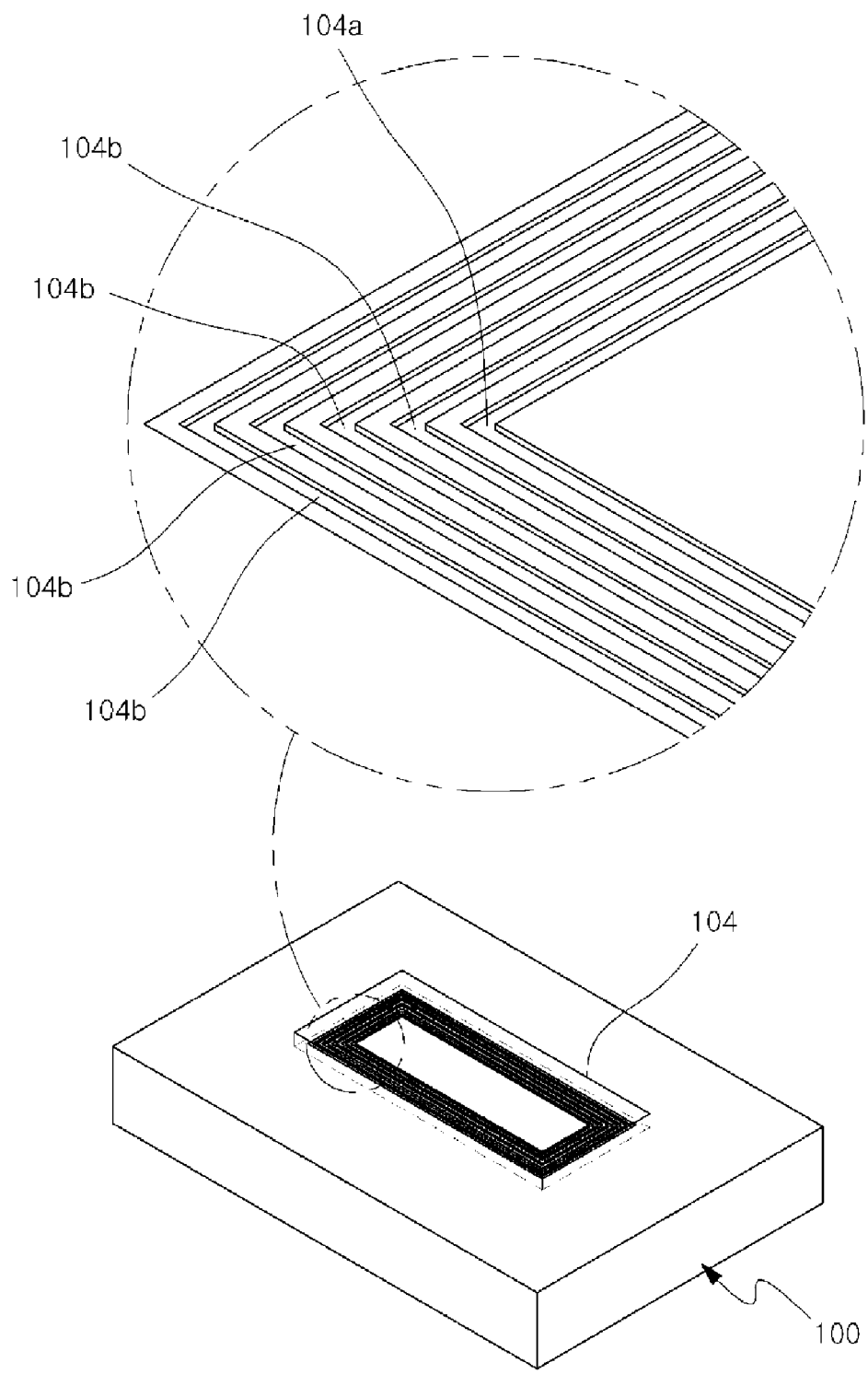
FIGS. 8 and 9 are partially-enlarged perspective views illustrating the pattern forming mold in accordance with the first embodiment.
Figure 9:
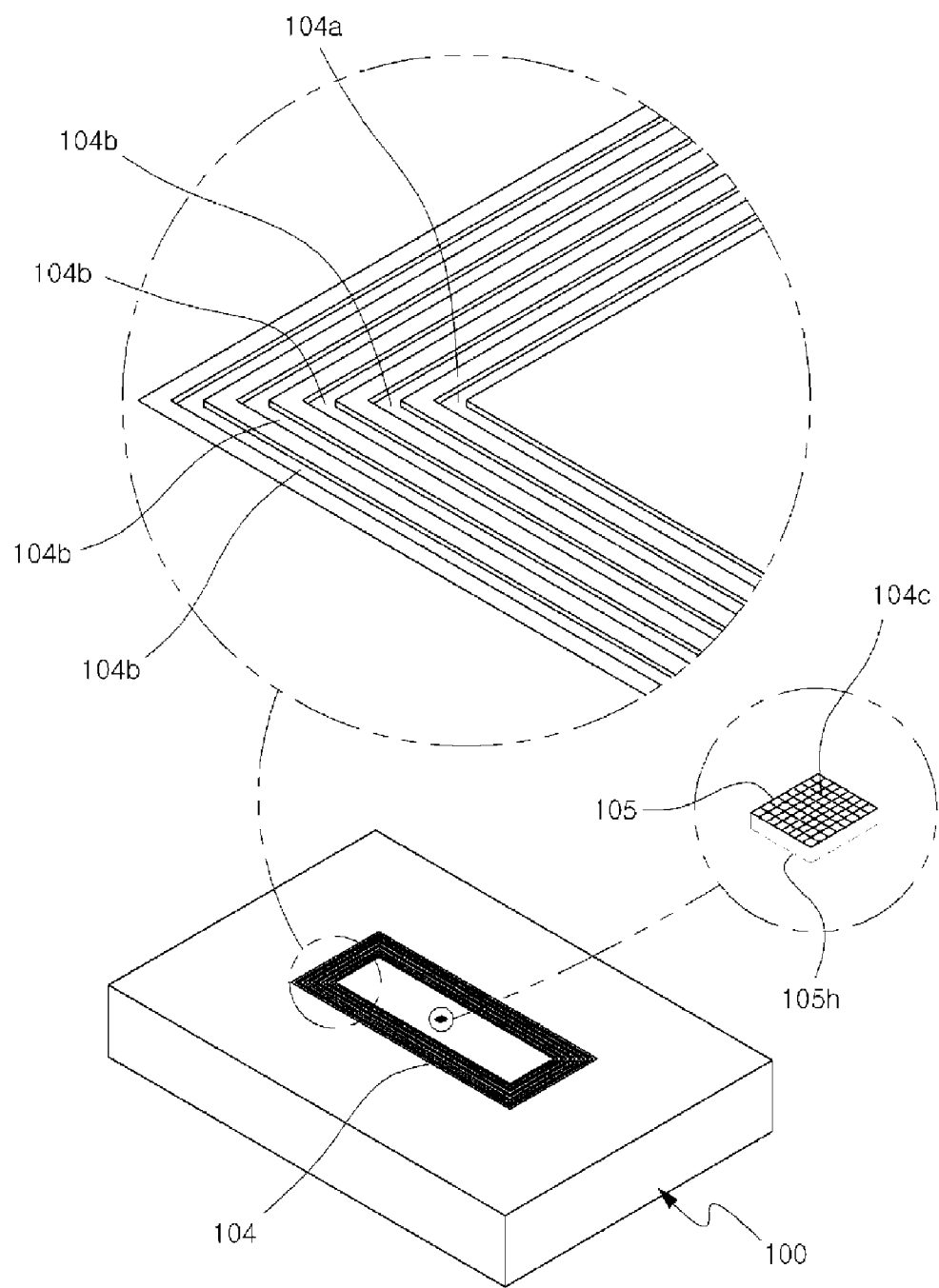

For example, as shown in FIGS. 8 and 9, the engraved pattern part 104 may be formed to include a sidewall pattern 104a which is formed through engraving to form the sidewall 210a of the charging chamber s, and a plurality of line patterns 104b which are spaced apart from one another by a predetermined interval outside the sidewall pattern 104a and are formed through engraving to form the plurality of line walls 210b outside the sidewall 210a of the charging chamber s.

Also, the engraved pattern part 104 may be formed by only the sidewall pattern 104a without the line patterns 104b, or may be formed in such a manner that the width of the sidewall 210a of the charging chamber s is increased by forming the entirety of the region remaining by excluding a region for forming the charging chamber s, through engraving. That is to say, the engraved pattern part 104 may be variously changed in its shape.

Figure 16:
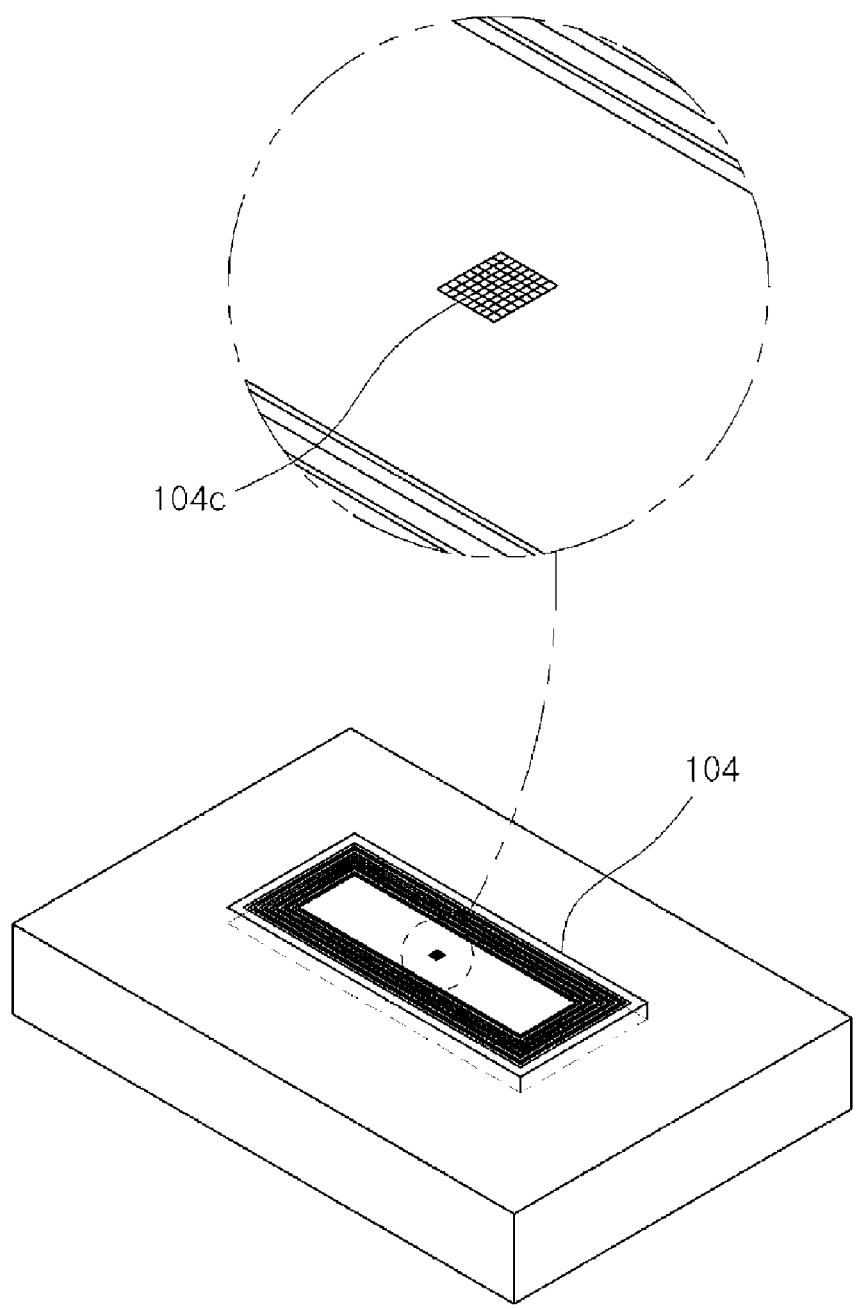
FIG. 16 is a perspective view illustrating a state in which a grid pattern is formed on an engraved pattern part in accordance with the first embodiment.
Figure 17:
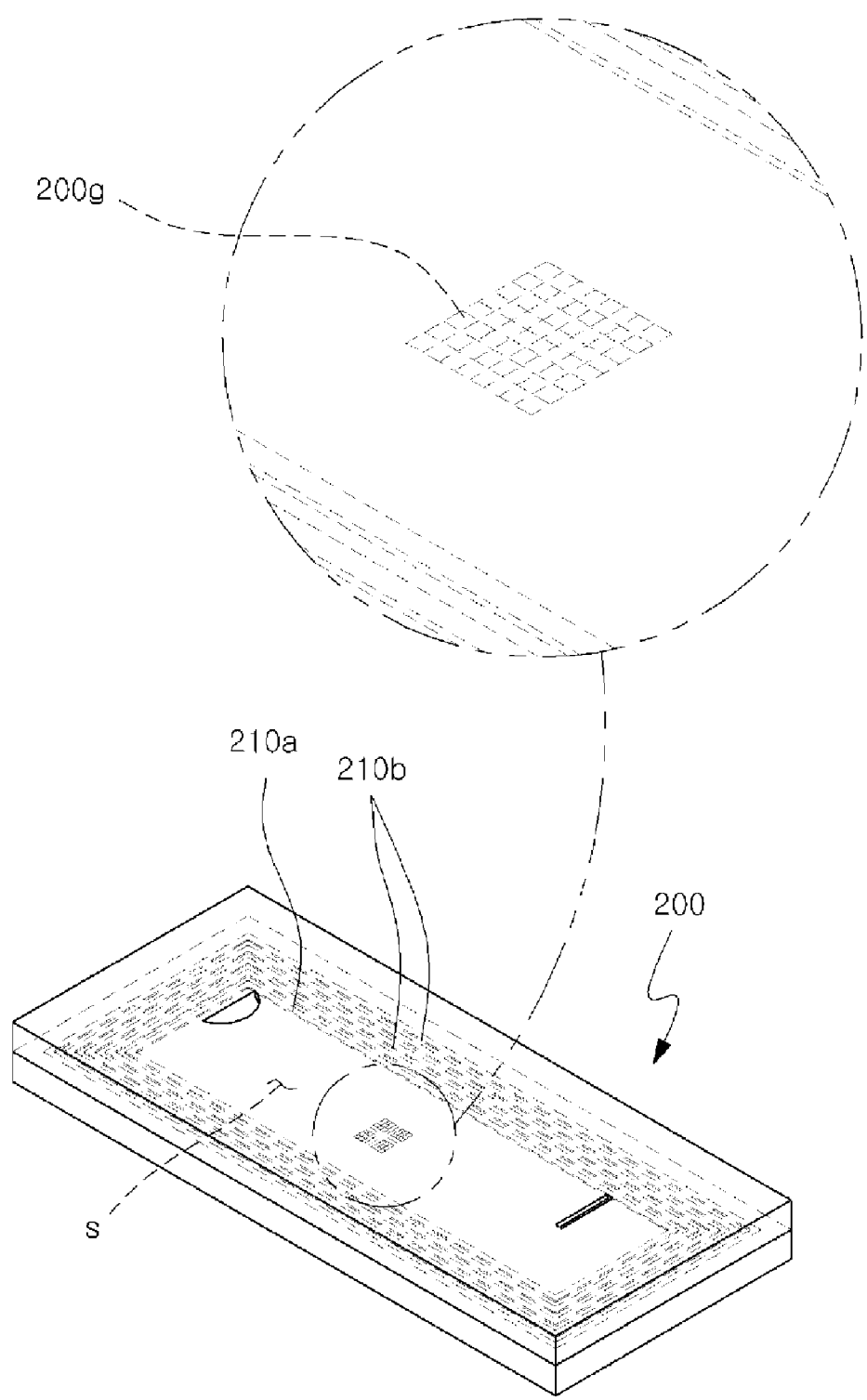
FIG. 17 is a perspective view illustrating the sample storage device which is formed with a grid pattern by the engraved pattern part having the grid pattern, in accordance with the first embodiment.

Meanwhile, as shown in FIGS. 16 and 17, the engraved pattern part 104 may be formed to include a grid pattern 104c for forming grid scales 200g, at a region inside the sidewall pattern 104a.

The grid pattern 104c may be formed through embossing or engraving at portions corresponding to the scale line portions of the grid scales 200g.

Figure 7A:
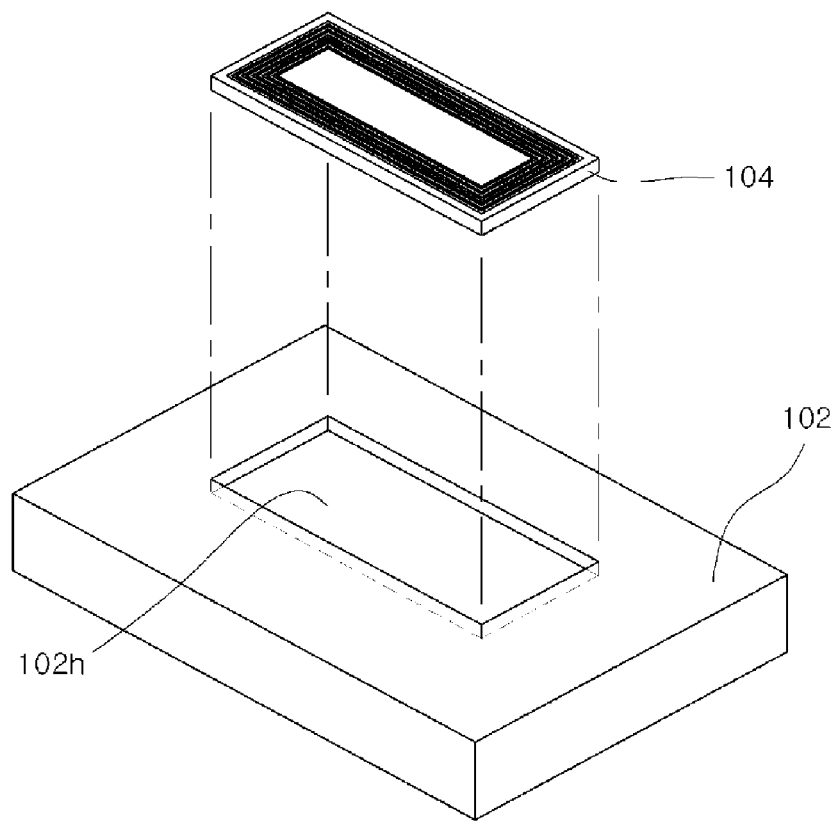
FIGS. 7a and 7b are perspective views illustrating a pattern forming mold in accordance with the first embodiment.
Figure 7B:
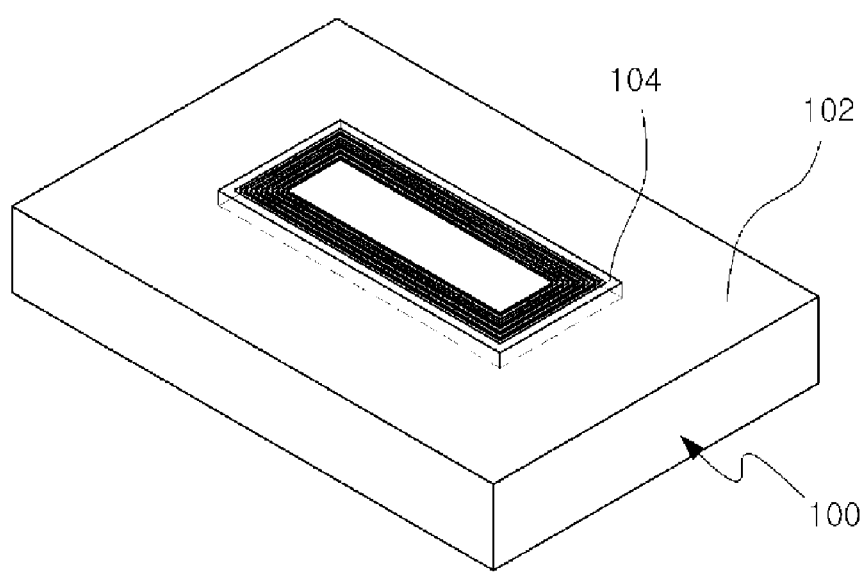

As shown in FIGS. 7a and 7b, the engraved pattern part 104 may be constructed by an electroformed mold 104 which has a pattern for forming the sidewall 210a of the charging chamber s. As the electroformed mold 104 is fixed to the upper surface of a pattern forming mold base 102, the pattern forming mold 100 may be constructed.

In other words, as shown in FIG. 7a, by defining a fixing groove 102h in which the electroformed mold 104 may be fixed, on the upper surface of the pattern forming mold base 102 and by inserting and fixing the electroformed mold 104 in the fixing groove 102h, the pattern forming mold 100 as shown in FIG. 7b may be constructed.

An electroformed mold refers to a mold which is fabricated by an electroforming method. Electroforming is a method of forming a metal layer to a predetermined thickness on the surface of a master fabricated through machining, by using electroplating, separating the formed metal layer, and forming the separated metal layer as a mold through finishing.

For example, an electroformed mold of a predetermined thickness may be fabricated by placing a metallic material for forming a mold and a master in a nickel sulfate aqueous solution in the same manner as in a plating method and connecting the metallic material with a positive electrode and the master with a negative electrode, to cause the metal particles of the metallic material connected to the positive electrode to migrate and cling to the surface of the master.

In the electroformed mold 104 as described above, since a mold may be formed to have a fine shape, it is easy to form the sidewall 210a of the charging chamber s which has a height and a thickness of a micro unit.

The electroformed mold 104 may be formed to include a grid pattern 104c for forming grid scales 200g, at a region inside the sidewall pattern 104a for forming the sidewall 210a of the charging chamber s.

Namely, the electroformed mold 104 may be formed to include all of the sidewall pattern 104a, the line patterns 104b and the grid pattern 104c.

Meanwhile, as shown in FIG. 9, the engraved pattern part 104 may be constructed as patterns for forming the sidewall 210a and the line walls 210b of the charging chamber s are etched on the upper surface of the pattern forming mold base 102.

The patterns may be formed through etching generally known in the art. For example, patterns for forming the sidewall 210a and the line walls 210b may be formed on the upper surface of the pattern forming mold base 102, by forming an oxide film on the upper surface of the pattern forming mold base 102, depositing a photosensitive resin on the oxide film, photosensitizing the photosensitive resin by radiating UV through a negative type mask, removing the photosensitized photosensitive resin, removing the oxide film at positions where the photosensitive resin is removed, removing the left photosensitive resin, and impregnating impurity gases at the positions where the oxide film does not exist.

The pattern forming mold 100 fabricated through etch-processing may be provided with a grid scale forming electroformed mold 105 for forming grid scales 200g, at a region inside the sidewall pattern 104a for forming the sidewall 210a of the charging chamber s.

The grid scales 200g formed at a region inside the sidewall 210a of the charging chamber s are formed to have a shape more fine than the sidewall 210a or the line walls 210b of the charging chamber s, and thus, it may be difficult to form patterns for forming the grid scales 200g, through etch-processing.

Therefore, after fabricating the grid scale forming electroformed mold 105 for forming the grid scales 200g, by an electroforming method capable of forming fine patterns, a groove 105h is defined at the region inside the sidewall pattern 104a of the etch-processed pattern forming mold 100, and the grid scale forming electroformed mold 105 is inserted into the groove 105h, by which the pattern forming mold 100 is constructed.

As described above, the engraved pattern part 104 may be formed on the upper surface of the pattern forming mold base 102 by fixing the electroformed mold 104 having the pattern for forming the sidewall 210a of the charging chamber s, to the upper surface of the pattern forming mold base 102, or by etch-processing the pattern for forming the sidewall 210a of the charging chamber s, on the upper surface of the pattern forming mold base 102, and through this, the pattern forming mold 100 may be prepared.

The step (b) will be described.

The step (b) is the step of pouring the predetermined amount of the liquid UV curable resin RS to be accommodated in the engraved pattern part 104, on the upper surface of the pattern forming mold 100.

Figure 10A:
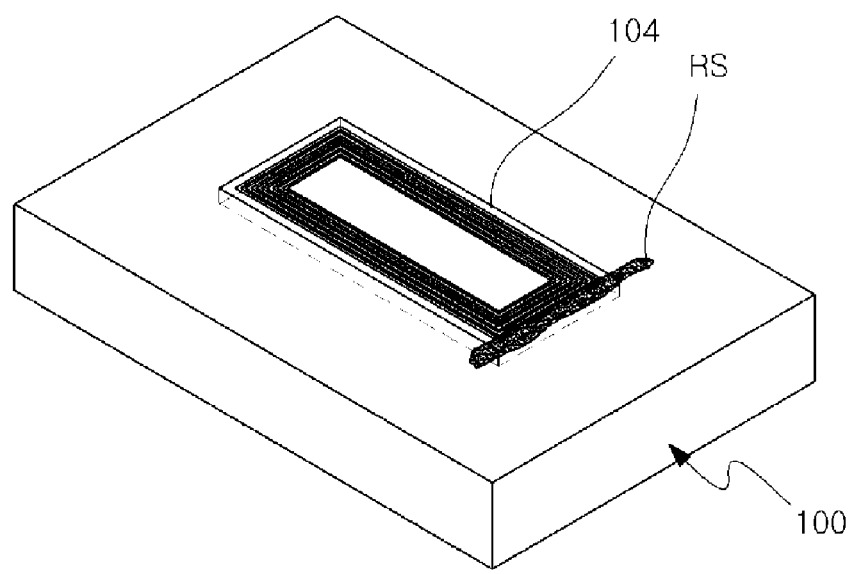
FIGS. 10a and 10b are perspective views illustrating states in which a liquid UV curable resin is supplied to the pattern forming mold in accordance with the first embodiment.

For example, as shown in FIG. 10a, the predetermined amount of the liquid UV curable resin RS capable of being entirely accommodated in the engraved pattern part 104 may be poured at one end of the engraved pattern part 104 on the upper surface of the pattern forming mold 100.

Figure 10B:
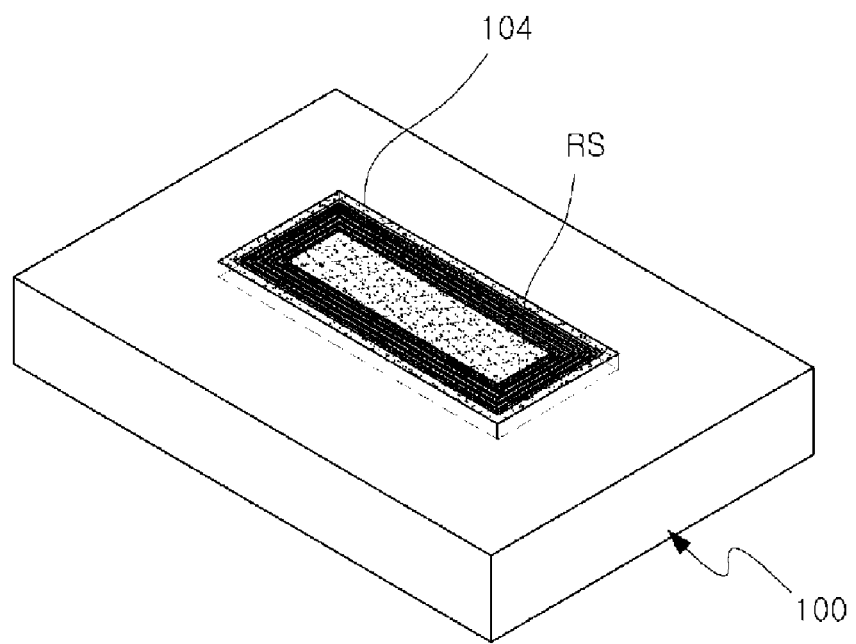

For another example, as shown in FIG. 10b, the liquid UV curable resin RS may be poured entirely on the upper surface of the pattern forming mold 100, in detail, entirely on the engraved pattern part 104, such that the liquid UV curable resin RS may be applied entirely to the engraved pattern part 104.

The liquid UV curable resin RS is a resin for forming the sidewall 210a and the line walls 210b of the charging chamber s. For example, as a urethane acrylate-based liquid UV curable resin generally known in the art, 'ND-938' of NANO PHOTONICS CHEMICAL CO., LTD may be used.

In order to increase the curability of the liquid UV curable resin RS, the liquid UV curable resin RS may be used by being mixed with a curing agent.

The step (c) will be described.

The step (c) is the step of seating the first light-transmitting substrate 210 on the upper surface of the pattern forming mold 100 and pressing them to each other.

Figure 11:
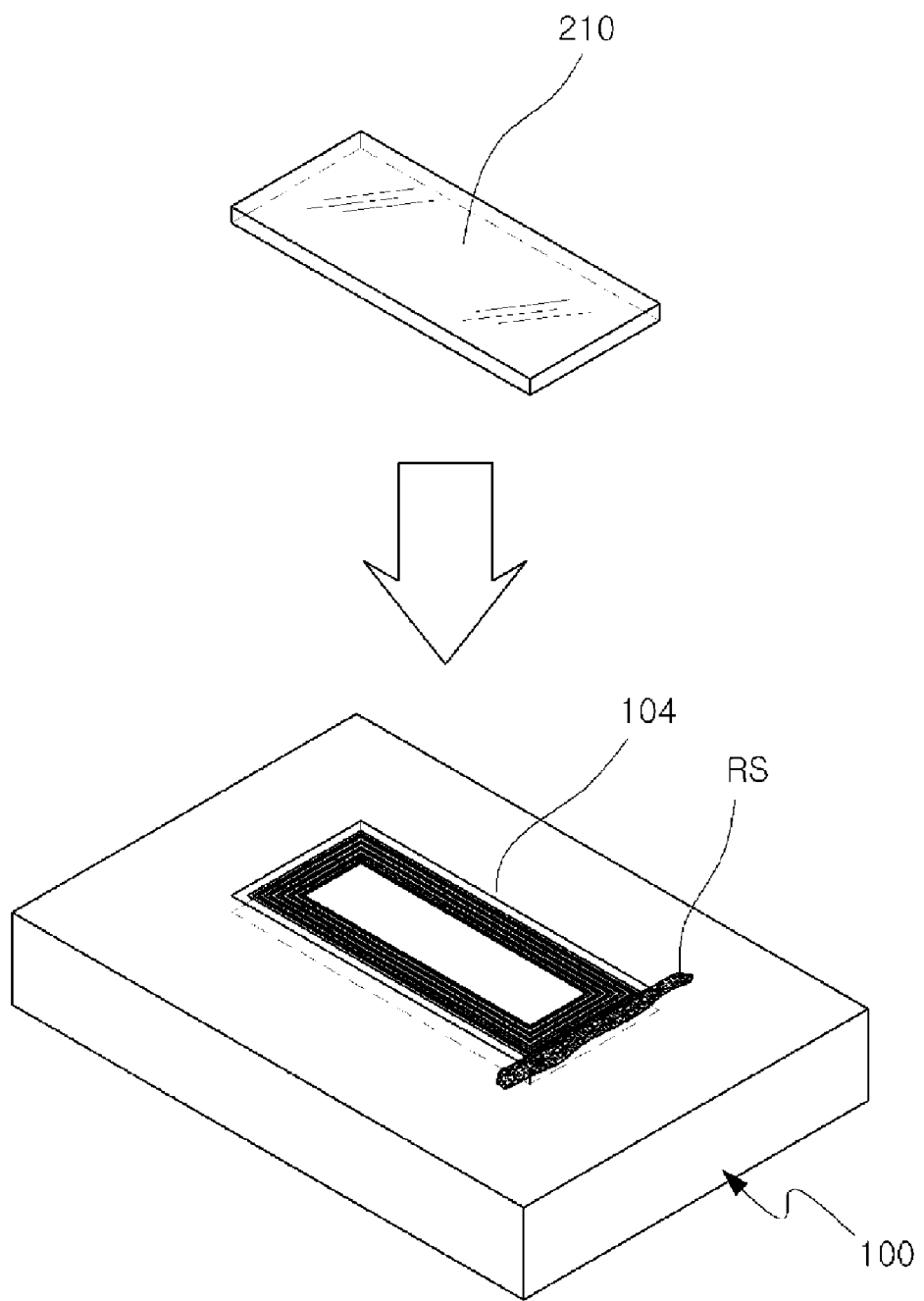
FIGS. 11 and 12 are perspective views illustrating the process of seating a first light-transmitting substrate on the upper surface of the pattern forming mold in accordance with the first embodiment.
Figure 12:
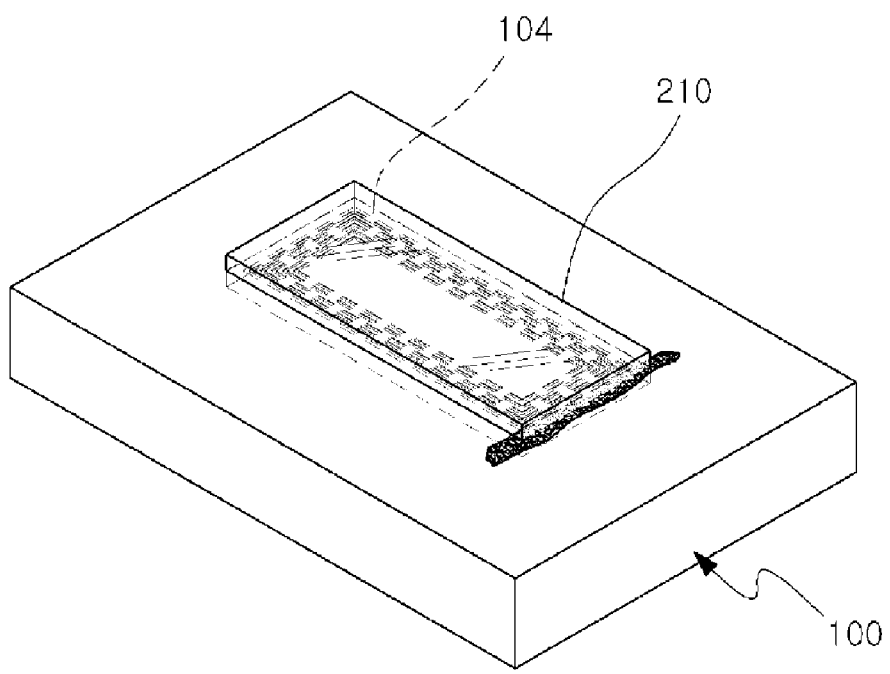

For example, as shown in FIGS. 11 and 12, in the state in which the predetermined amount of the liquid UV curable resin RS is poured at one end of the engraved pattern part 104 on the upper surface of the pattern forming mold 100, the first light-transmitting substrate 210 may be aligned with and seated on the upper surface of the pattern forming mold 100.

The pressing of the pattern forming mold 100 and the first light-transmitting substrate 210 to each other may be carried out by the deadweight of the first light-transmitting substrate 210 or by separate pressing means.

Figure 13:
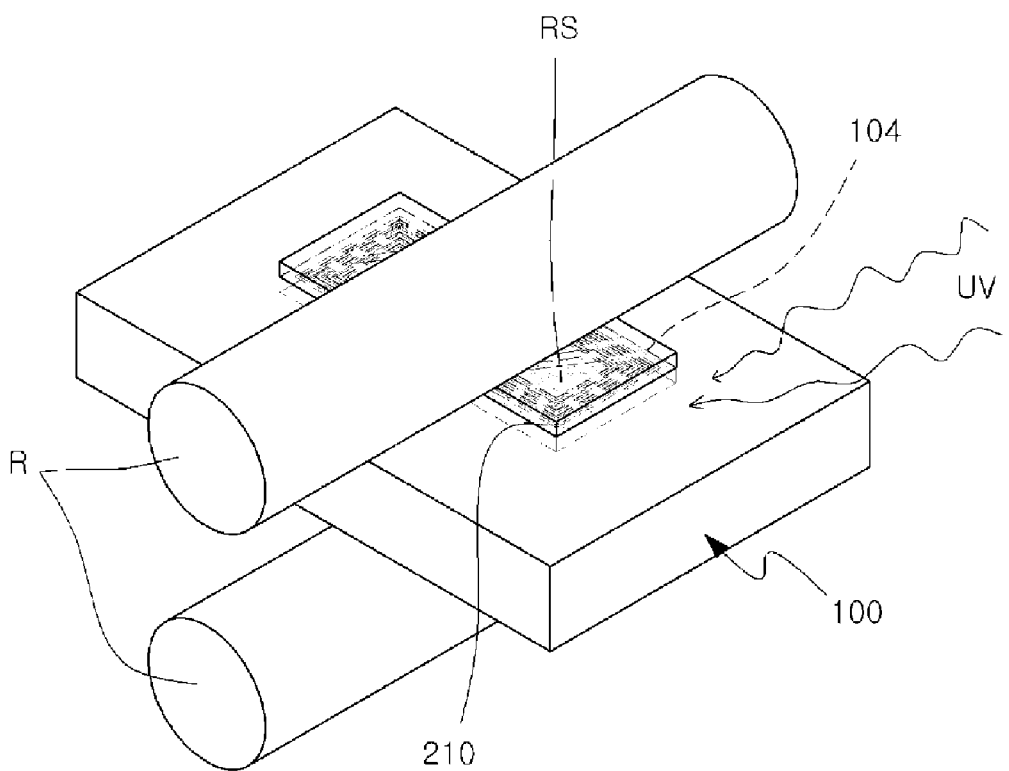
FIG. 13 is a perspective view illustrating the processes of pressing the pattern forming mold and the first light-transmitting substrate and radiating ultraviolet in accordance with the first embodiment.

For example, as shown in FIG. 13, the pattern forming mold 100 and the first light-transmitting substrate 210 may be pressed to each other as they pass through between a pair of pressing rollers R from the end of the engraved pattern part 104 where the liquid UV curable resin RS is poured.

Besides, other pressing means known in the art may be optionally applied so long as it is possible to press the pattern forming mold 100 and the first light-transmitting substrate 210 to each other.

Through the above-described pressing process, the liquid UV curable resin RS may exist in the form of a film with a thickness of approximately 3 µm between the embossed portions of the engraved pattern part 104 of the pattern forming mold 100 and the first light-transmitting substrate 210, and the liquid UV curable resin RS is filled in correspondence to the engraved patterns between the engraved portions of the engraved pattern part 104 of the pattern forming mold 100 and the first light-transmitting substrate 210.

The height of the engraved portions may be set to approximately 10 µm to 100 µm as the height of the charging chamber s.

The step (d) will be described.

The step (d) is the step of radiating UV with the liquid UV curable resin RS accommodated in the engraved pattern part 104 and thereby curing the liquid UV curable resin RS.

That is to say, the step (d) may be performed after the pattern forming mold 100 and the first light-transmitting substrate 210 pass through the pair of pressing rollers R.

For example, as shown in FIG. 13, as the pattern forming mold 100 and the first light-transmitting substrate 210 pass through the pair of pressing rollers R from the end of the engraved pattern part 104 where the liquid UV curable resin RS is poured, the liquid UV curable resin RS may be evenly distributed wholly between the pattern forming mold 100 and the first light-transmitting substrate 210 and may be accommodated in the engraved pattern part 104.

As UV is radiated toward a discharge side through which the pattern forming mold 100 and the first light-transmitting substrate 210 pass through the pair of pressing rollers R and are then discharged, the liquid UV curable resin RS evenly distributed between the pattern forming mold 100 and the first light-transmitting substrate 210 may be cured.

The step (e) will be described.

The step (e) is the step of separating the first light-transmitting substrate 210 which has the sidewall 210a formed as the liquid UV curable resin RS is cured, from the pattern forming mold 100.

The pattern forming mold 100 may be release-processed such that the cured resin may be easily released. For example, the pattern forming mold 100 may be release-processed through annealing, plating, deposition coating, etc.

Therefore, the first light-transmitting substrate 210 having the sidewall 210a which is formed as the liquid UV curable resin RS is cured may be easily separated from the pattern forming mold 100.

The step (f) will be described.

The step (f) is the step of forming the charging chamber s by adhering the second light-transmitting substrate 220 to the surface of the first light-transmitting substrate 210 on which the sidewall 210a is formed.

As shown in FIG. 14, the second light-transmitting substrate 220 is formed to have substantially the same area as the first light-transmitting substrate 210, and is formed with the introducing part 220a for charging a sample into the charging chamber s and the discharging part 220b for discharging the sample or air.

The first light-transmitting substrate 210 and the second light-transmitting substrate 220 may be adhered to each other by stacking them through applying a UV curable adhesive between them excluding a region corresponding to the charging chamber s and then radiating UV.

For example, the UV curable adhesive may be applied to be filled in the spaces between some line walls 210b. When adhering the first light-transmitting substrate 210 and the second light-transmitting substrate 220, as the UV curable adhesive filled in the spaces between some line walls 210b flows into the spaces between neighboring line walls 210b and is thus evenly distributed wholly, it is possible to prevent the UV curable adhesive from leaking to an outside through the pair of substrates.

The UV curable adhesive as a liquid substance including, for example, urethane acrylate, is generally referred to as 'liquid UV', and has a characteristic that it is cured when heat is applied or UV is radiated.

In order to increase the curability of the liquid UV curable adhesive, the liquid UV curable adhesive may be used by being mixed with a curing agent.

As the first light-transmitting substrate 210 and the second light-transmitting substrate 220 are adhered as described above, as shown in FIG. 15, the sample storage device 200 having the charging chamber s may be completed.

SECOND EMBODIMENT

Figure 5:
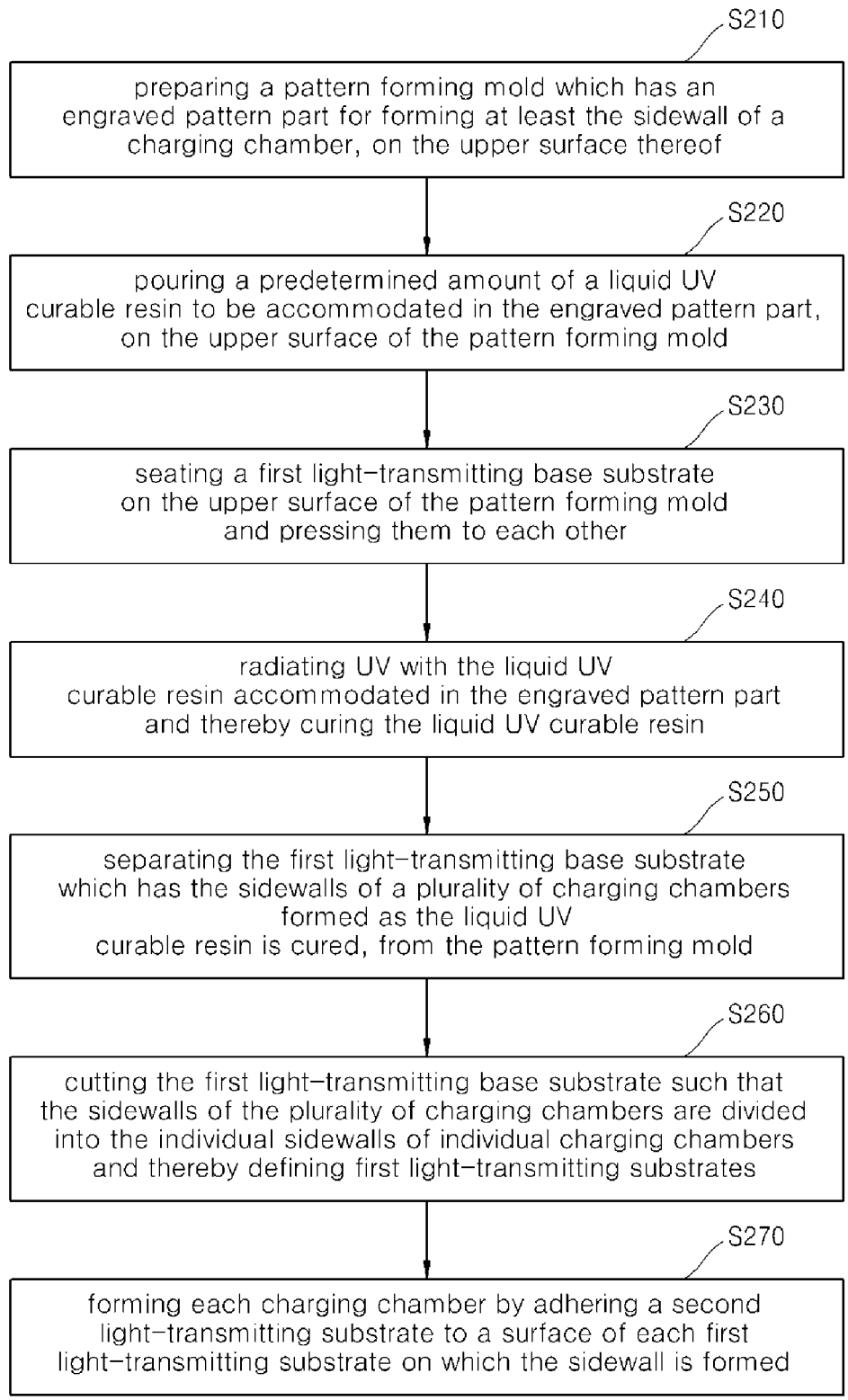
FIG. 5 is a flow chart explaining a method for manufacturing a sample storage device in accordance with a second embodiment.

As shown in FIG. 5, a method for manufacturing a sample storage device in accordance with a second embodiment includes (a) preparing a pattern forming mold which has an engraved pattern part for forming at least the sidewall of a charging chamber, on the upper surface thereof, the engraved pattern part being formed such that a plurality of pattern parts each of which forms the sidewall of a single charging chamber are arranged therein and thereby form the sidewalls of a plurality of charging chambers; (b) pouring a predetermined amount of a liquid UV curable resin to be accommodated in the engraved pattern part, on the upper surface of the pattern forming mold; (c) seating a first light-transmitting base substrate on the upper surface of the pattern forming mold and pressing them to each other; (d) radiating UV with the liquid UV curable resin accommodated in the engraved pattern part and thereby curing the liquid UV curable resin; (e) separating the first light-transmitting base substrate which has the sidewalls of the plurality of charging chambers formed as the liquid UV curable resin is cured, from the pattern forming mold; (f) cutting the first light-transmitting base substrate such that the sidewalls of the plurality of charging chambers are divided into the individual sidewalls of individual charging chambers and thereby defining first light-transmitting substrates; and (g) forming each charging chamber by adhering a second light-transmitting substrate to a surface of each first light-transmitting substrate on which the sidewall is formed.

First, the step (a) will be described.

The step (a) is the step of preparing a pattern forming mold 100 which has an engraved pattern part 104 for forming at least the sidewall 210*a* of the charging chamber s, on the upper surface thereof, and the engraved pattern part 104 is formed such that a plurality of pattern parts 104' each of which forms the sidewall 210*a* of a single charging chamber s are arranged therein and thereby form the sidewalls 210*a* of a plurality of charging chambers s.

Figure 18A:
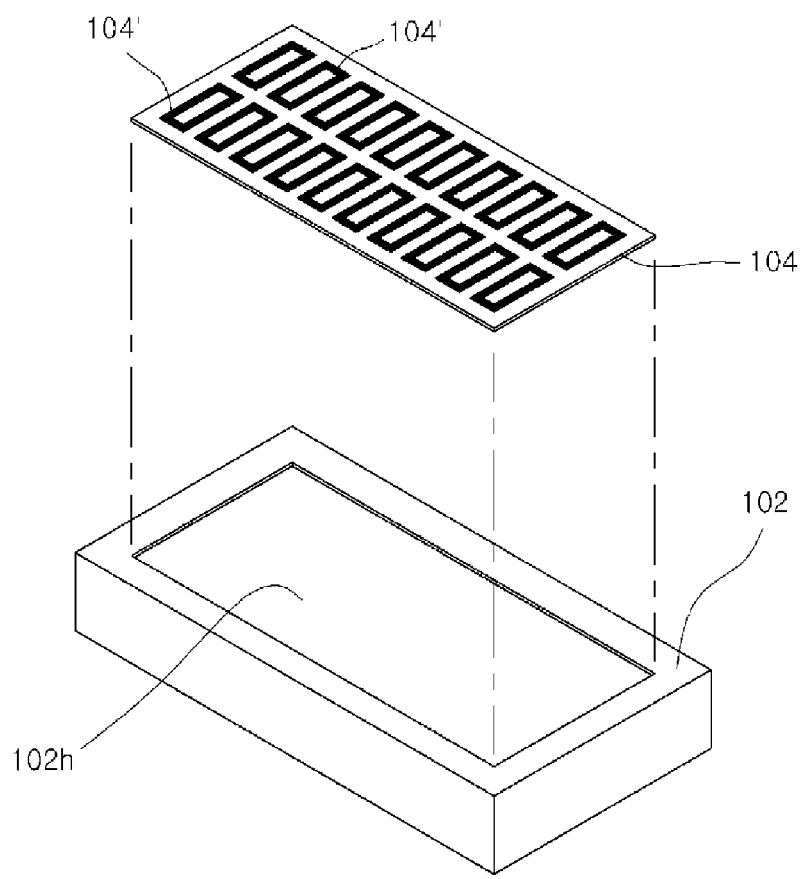
FIGS. 18a and 18b are perspective views illustrating a pattern forming mold in accordance with a second embodiment.
Figure 18B:
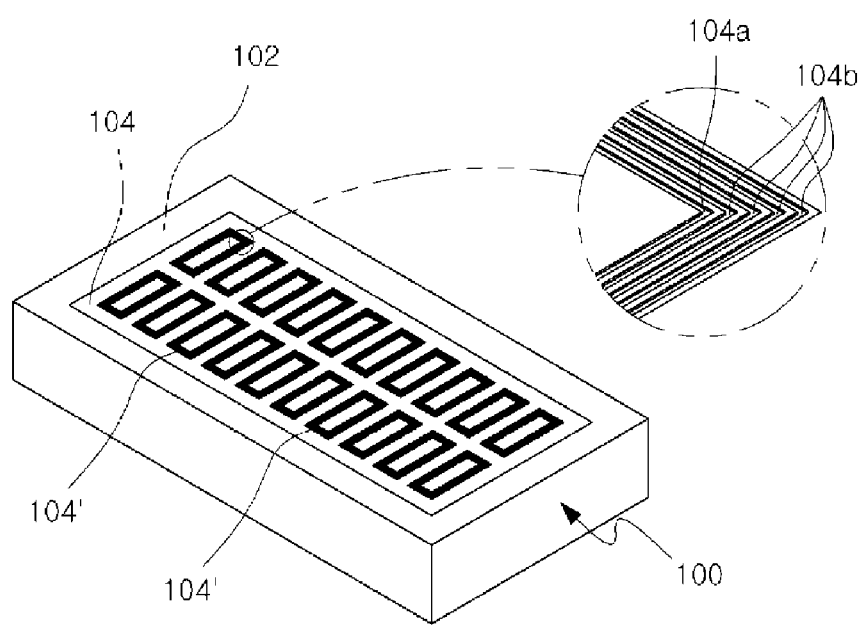
Figure 19:
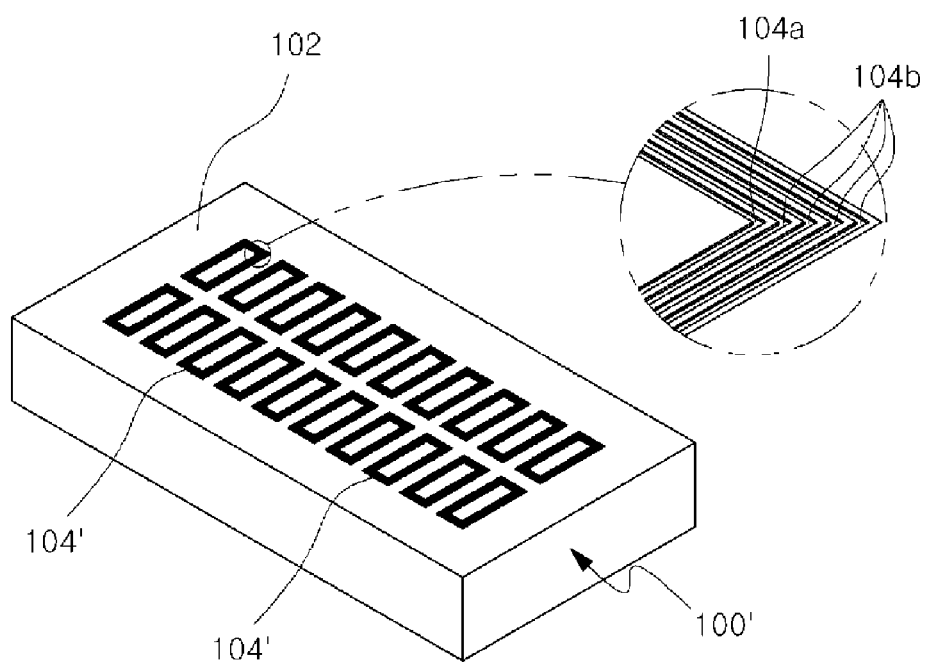
FIG. 19 is a perspective view illustrating another pattern forming mold in accordance with the second embodiment.

For example, as shown in FIGS. 18*a*, 18*b* and 19, the engraved pattern part 104 may be formed such that the pattern parts 104' each of which forms the sidewall 210*a* of a single charging chamber s are arranged in the form of 2×10. Each pattern part 104' forms the sidewall 210*a* of the charging chamber s of one sample storage device.

In other words, the engraved pattern part 104 according to the second embodiment is constructed in such a manner that the plurality of pattern parts 104' are arranged to be capable of simultaneously forming the sidewalls 210*a* of the charging chambers s of a plurality of sample storage devices. Since a plurality of sample storage devices may be manufactured through one time manufacturing process by using such an engraved pattern part 104, mass production is made possible.

The pattern parts 104' which form the engraved pattern part 104 may be formed into various patterns to form various shapes outside the charging chambers s including the sidewalls 210*a* of the charging chambers s.

For example, as shown in FIGS. 18*a*, 18*b* and 19, each of the pattern parts 104' may be formed to include a sidewall pattern 104*a*, line patterns 104*b* and a grid pattern (not shown). Since the detailed pattern shapes are the same as or similar to the shapes of the sidewall pattern 104*a*, the line patterns 104*b* and the grid pattern 104*c* of the engraved pattern part 104 according to the first embodiment, repeated descriptions thereof will be omitted herein.

Also, similarly to the engraved pattern part 104 according to the first embodiment, in the case of the engraved pattern part 104 according to the second embodiment, for example, as shown in FIGS. 18*a* and 18*b*, the pattern forming mold 100 may be constructed by disposing an electroformed mold 104 on the upper surface of a pattern forming mold base 102, or, as shown in FIG. 19, the pattern forming mold 100 may be constructed by forming patterns on the upper surface of a pattern forming mold base 102 through etch-processing. Repeated descriptions thereof will be omitted.

The step (b) will be described.

The step (b) is the step of pouring the predetermined amount of the liquid UV curable resin RS to be accommodated in the engraved pattern part 104, on the upper surface of the pattern forming mold 100.

Figure 20A:
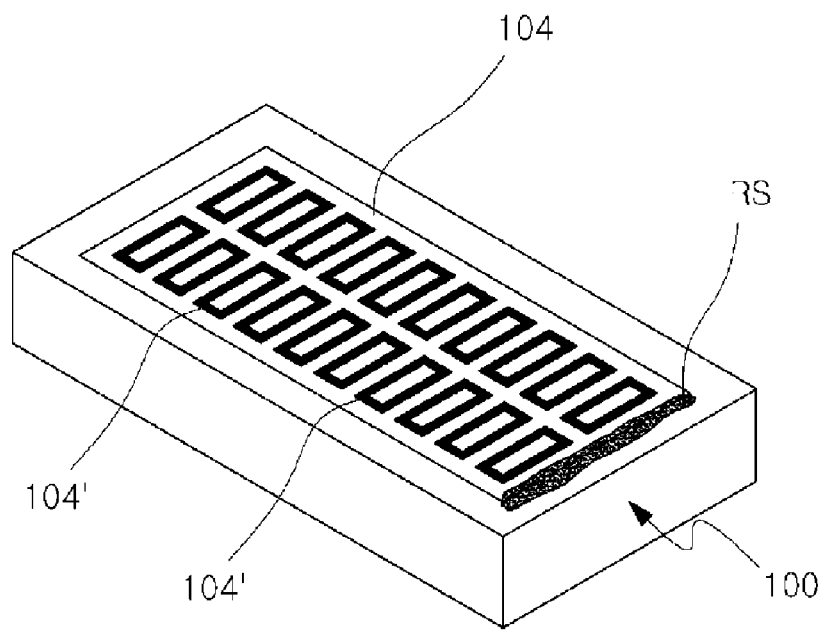
FIGS. 20a and 20b are perspective views illustrating states in which a liquid UV curable resin is supplied to the pattern forming mold in accordance with the second embodiment.
Figure 20B:
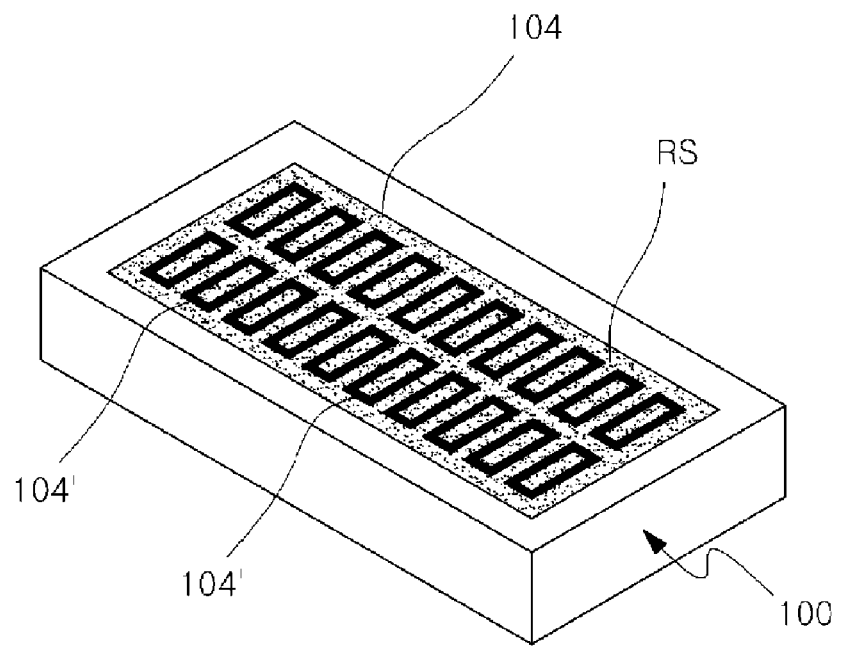

For example as shown in FIG. 20*a*, the predetermined amount of the liquid UV curable resin RS capable of being entirely accommodated in the engraved pattern part 104 may be poured at one end of the engraved pattern part 104 on the upper surface of the pattern forming mold 100, or, as shown in FIG. 20*b*, the liquid UV curable resin RS may be poured entirely on the upper surface of the pattern forming mold 100, in detail, entirely on the engraved pattern part 104, such that the liquid UV curable resin RS may be applied entirely to the engraved pattern part 104.

The liquid UV curable resin RS is a resin for forming the sidewall 210*a* and the line walls 210*b* of the charging chamber s. For example, as a urethane acrylate-based liquid UV curable resin generally known in the art, 'ND-938' of NANO PHOTONICS CHEMICAL CO., LTD may be used.

The step (c) will be described.

The step (c) is the step of seating a first light-transmitting base substrate 210' on the upper surface of the pattern forming mold 100 and pressing them to each other.

Figure 21:
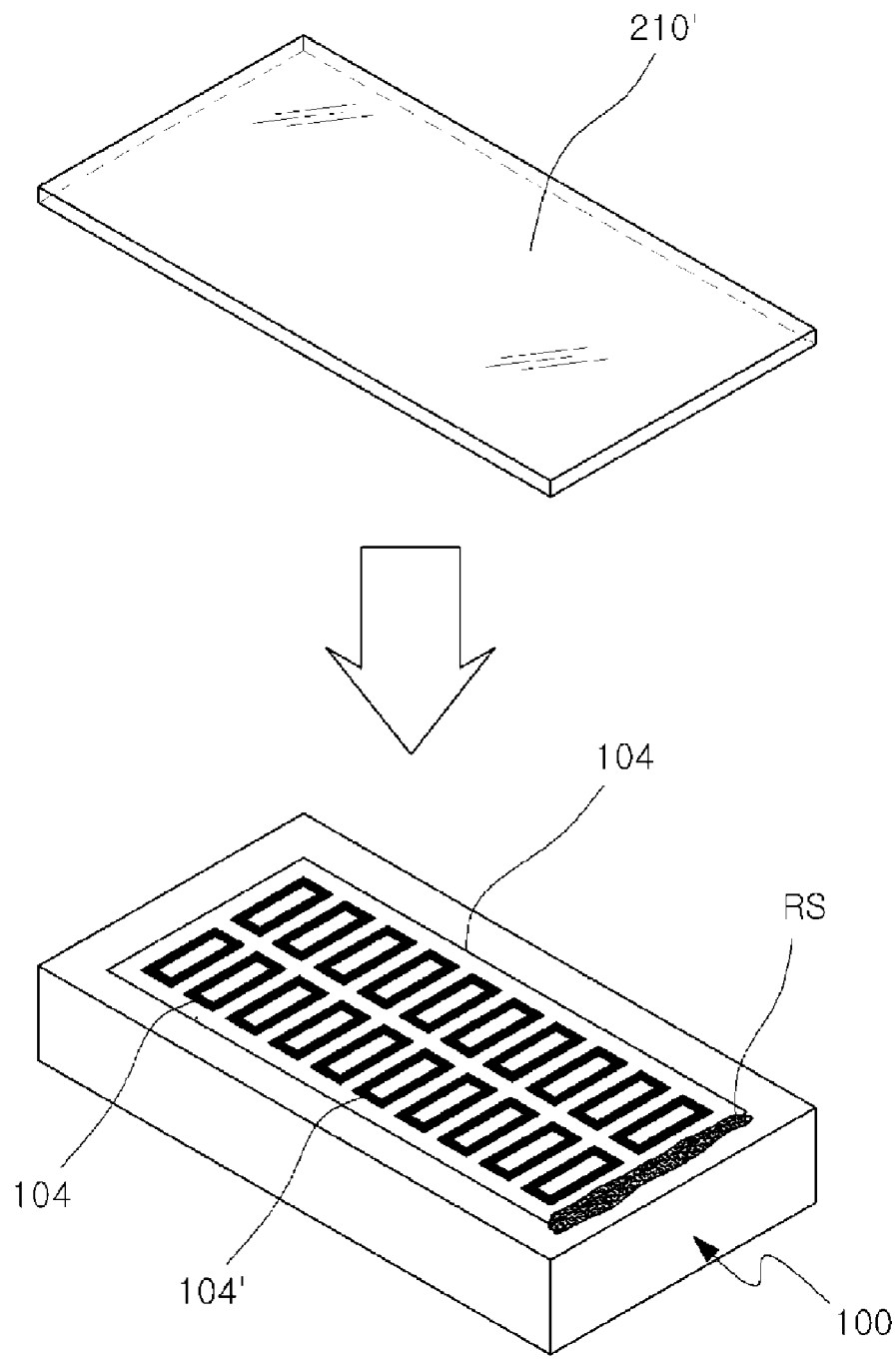
FIGS. 21 and 22 are perspective views illustrating the process of seating a first light-transmitting base substrate on the upper surface of the pattern forming mold in accordance with the second embodiment.
Figure 22:
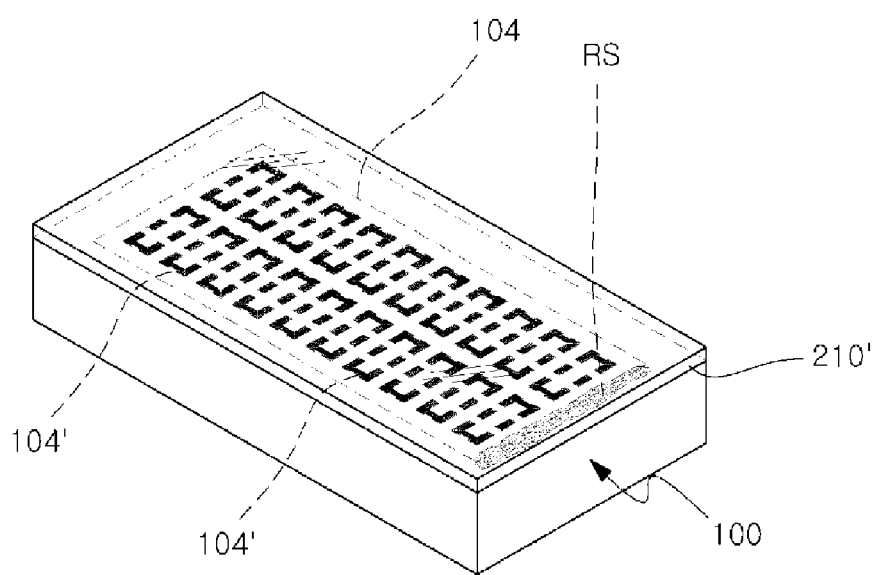

For example, as shown in FIGS. 21 and 22, in the state in which the predetermined amount of the liquid UV curable resin RS is poured at one end of the engraved pattern part 104 on the upper surface of the pattern forming mold 100, the first light-transmitting base substrate 210' may be aligned with and seated on the upper surface of the pattern forming mold 100.

Figure 23:
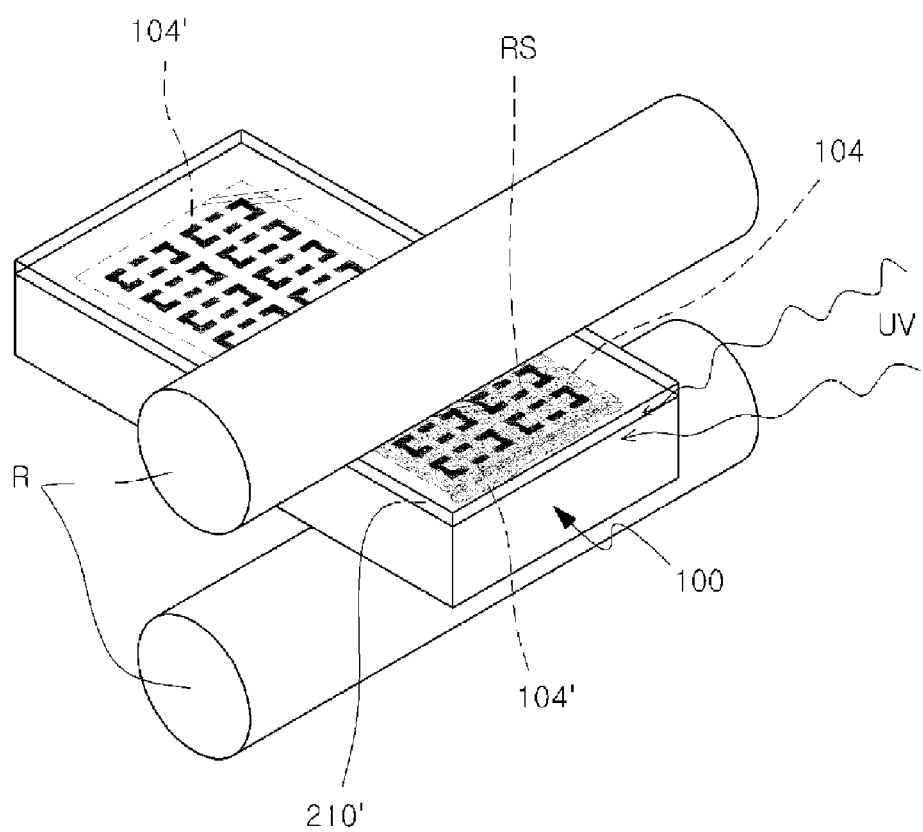
FIG. 23 is a perspective view illustrating the processes of pressing the pattern forming mold and the first light-transmitting base substrate and radiating ultraviolet in accordance with the second embodiment.

For example, as shown in FIG. 23, the pressing of the pattern forming mold 100 and the first light-transmitting base substrate 210' to each other may be carried out as they pass through between a pair of pressing rollers R from the end of the engraved pattern part 104 where the liquid UV curable resin RS is poured.

Besides, other pressing means known in the art may be optionally applied so long as it is possible to press the pattern forming mold 100 and the first light-transmitting base substrate 210' to each other.

Through the above-described pressing process, the liquid UV curable resin RS may exist in the form of a film with a thickness of approximately 3 μm between the embossed portions of the engraved pattern part 104 of the pattern forming mold 100 and the first light-transmitting base substrate 210', and the liquid UV curable resin RS is filled in correspondence to the engraved patterns between the engraved portions of the engraved pattern part 104 of the pattern forming mold 100 and the first light-transmitting base substrate 210'.

The height of the engraved portions may be set to approximately 10 μm to 100 μm as the height of the charging chamber s.

The step (d) will be described.

The step (d) is the step of radiating UV with the liquid UV curable resin RS accommodated in the engraved pattern part 104 and thereby curing the liquid UV curable resin RS.

That is to say, the step (d) may be performed after the pattern forming mold 100 and the first light-transmitting base substrate 210' pass through the pair of pressing rollers R.

For example, as shown in FIG. 23, as the pattern forming mold 100 and the first light-transmitting base substrate 210' pass through the pair of pressing rollers R from the end of the engraved pattern part 104 where the liquid UV curable resin RS is poured, the liquid UV curable resin RS may be evenly distributed wholly between the pattern forming mold 100 and the first light-transmitting base substrate 210' and may be accommodated in the engraved pattern part 104.

As UV is radiated toward a discharge side through which the pattern forming mold 100 and the first light-transmitting base substrate 210' pass through the pair of pressing rollers R and are then discharged, the liquid UV curable resin RS evenly distributed between the pattern forming mold 100 and the first light-transmitting base substrate 210' may be cured.

The step (e) will be described.

The step (e) is the step of separating the first light-transmitting base substrate 210' which has the sidewalls 210a of the plurality of charging chambers s formed as the liquid UV curable resin RS is cured, from the pattern forming mold 100.

The pattern forming mold 100 may be release-processed such that the cured resin may be easily released. For example, the pattern forming mold 100 may be release-processed through annealing, plating, deposition coating, etc.

Therefore, the first light-transmitting base substrate 210' having the sidewalls 210a which are formed as the liquid UV curable resin RS is cured may be easily separated from the pattern forming mold 100.

The step (f) will be described.

The step (f) is the step of cutting the first light-transmitting base substrate 210' such that the sidewalls 210a of the plurality of charging chambers s are divided into the individual sidewalls 210a of individual charging chambers s and thereby defining first light-transmitting substrates 210.

Figure 24:
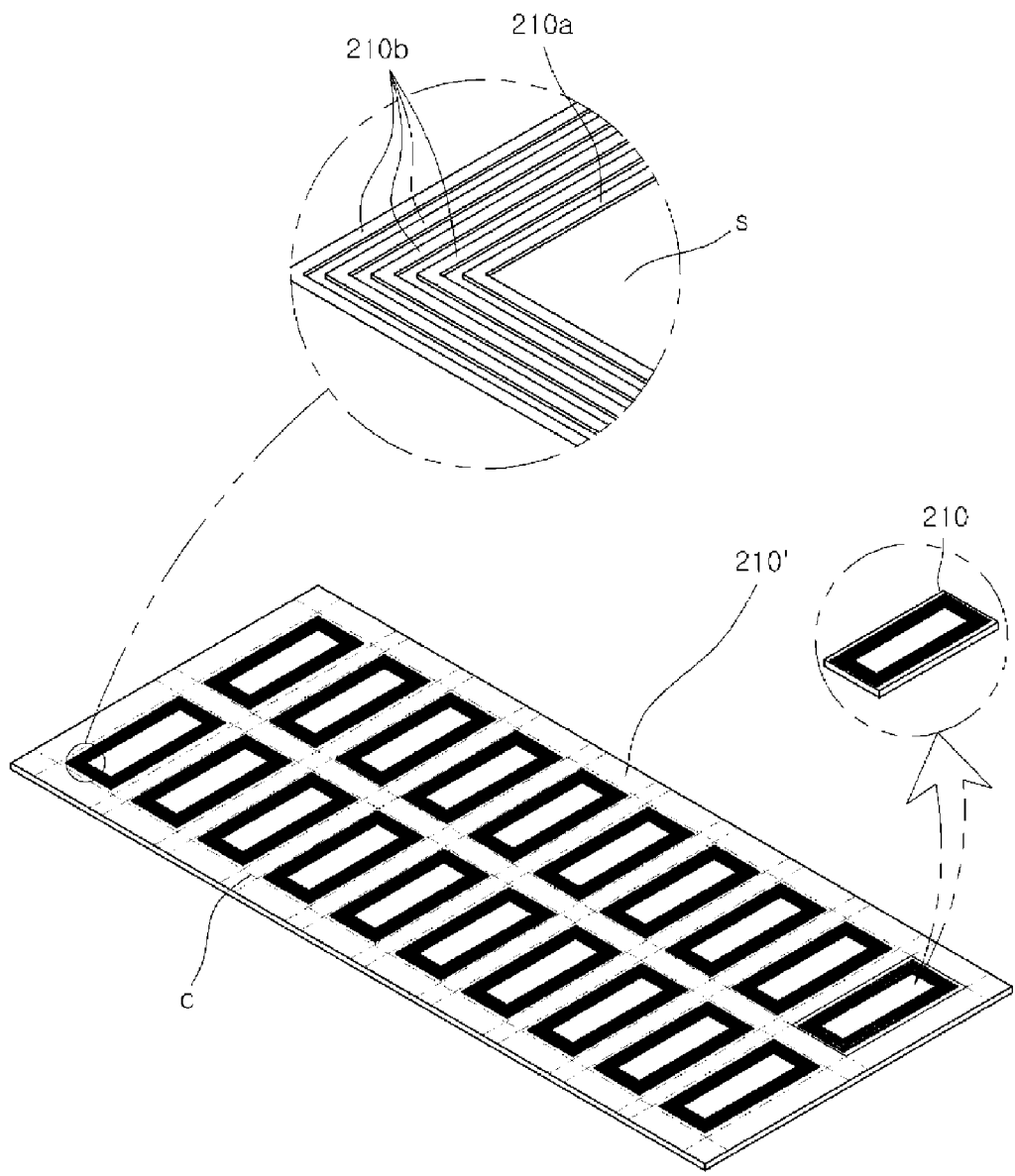
FIG. 24 is a perspective view illustrating the first light-transmitting base substrate which is formed with a plurality of charging chamber sidewalls, in accordance with the second embodiment.

For example, as shown in FIG. 24, on one surface of the first light-transmitting base substrate 210' which is formed through the above steps (a) to (e), the sidewalls 210a and the line walls 210b which form the individual charging chambers s are arranged in the form of 2×10.

By cutting the first light-transmitting base substrate 210' along imaginary cutting lines c, the first light-transmitting substrates 210 are defined.

The cutting of the first light-transmitting base substrate 210' may be carried out in a mechanical cutting scheme such as Thomson cutting, NC cutting, etc.

Therefore, similarly to the first light-transmitting substrate 210 according to the first embodiment shown in FIG. 14, on one surface of each of the first light-transmitting substrates 210 which are formed as the first light-transmitting base substrate 210' is cut, one sidewall 210a and the plurality of line walls 210b which form one charging chamber s may be provided.

The step (g) will be described.

The step (g) is the step of forming the charging chamber s by adhering the second light-transmitting substrate 220 to the surface of the first light-transmitting substrate 210 on which the sidewall 210a is formed.

The second light-transmitting substrate 220 (see FIG. 14) is formed to have substantially the same area as the first light-transmitting substrate 210, and is formed with the introducing part 220a for charging a sample into the charging chamber s and the discharging part 220b for discharging the sample or air.

The first light-transmitting substrate 210 and the second light-transmitting substrate 220 may be adhered to each other by stacking them through applying a UV curable adhesive between them excluding a region corresponding to the charging chamber s and then radiating UV. Since a detailed adhering method is the same as in the first embodiment, repeated descriptions will be omitted herein.

As the first light-transmitting substrate 210 and the second light-transmitting substrate 220 are adhered as described above, as in the sample storage device according to the first embodiment shown in FIG. 15, a single sample storage device may be completed.

THIRD EMBODIMENT

Figure 6:
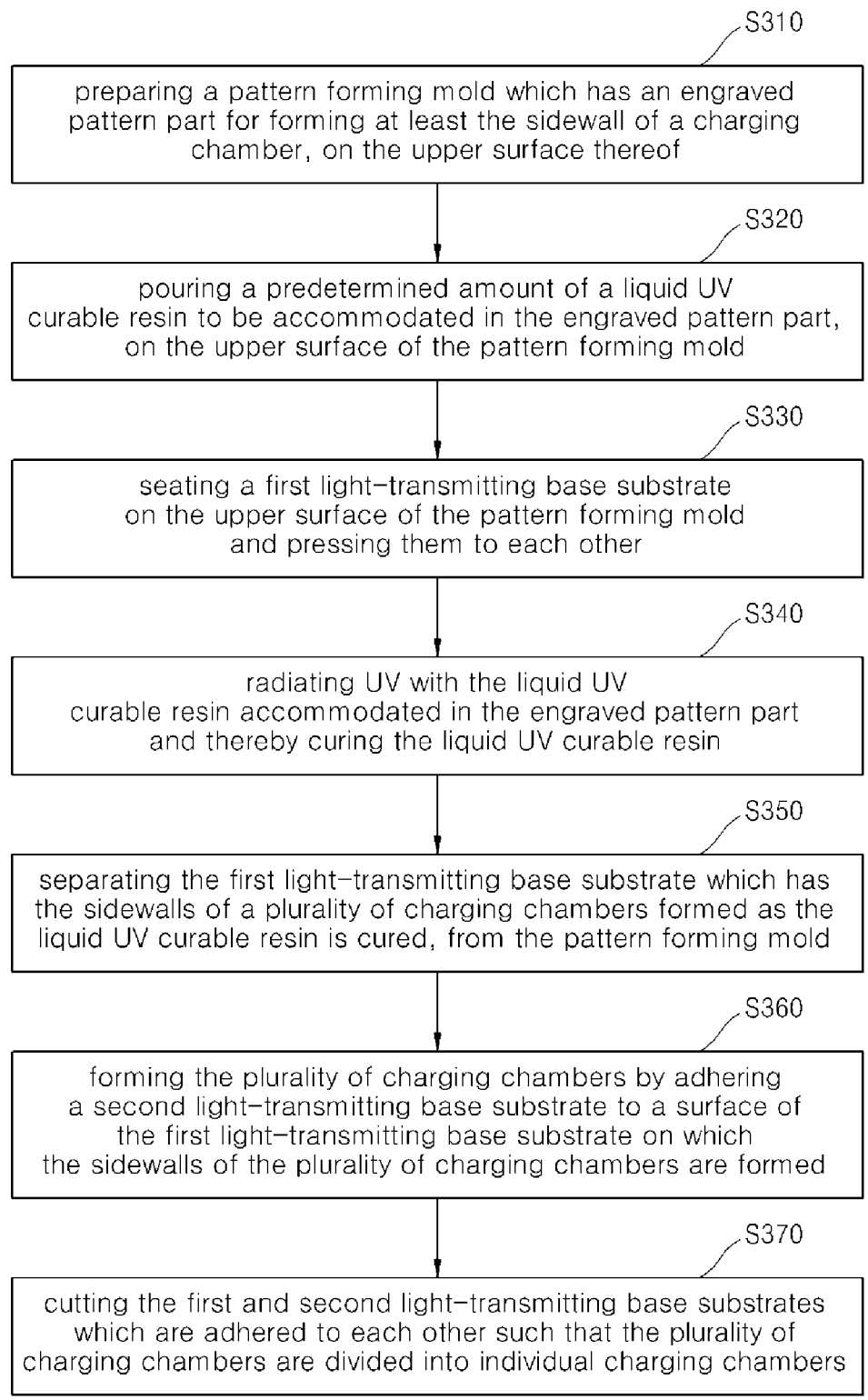
FIG. 6 is a flow chart explaining a method for manufacturing a sample storage device in accordance with a third embodiment.

As shown in FIG. 6, a method for manufacturing a sample storage device in accordance with a third embodiment includes (a) preparing a pattern forming mold which has an engraved pattern part for forming at least the sidewall of a charging chamber, on the upper surface thereof, the engraved pattern part being formed such that a plurality of pattern parts each of which forms the sidewall of a single charging chamber are arranged therein and thereby form the sidewalls of a plurality of charging chambers; (b) pouring a predetermined amount of a liquid UV curable resin to be accommodated in the engraved pattern part, on the upper surface of the pattern forming mold; (c) seating a first light-transmitting base substrate on the upper surface of the pattern forming mold and pressing them to each other; (d) radiating UV with the liquid UV curable resin accommodated in the engraved pattern part and thereby curing the liquid UV curable resin; (e) separating the first light-transmitting base substrate which has the sidewalls of the plurality of charging chambers formed as the liquid UV curable resin is cured, from the pattern forming mold; (f) forming the plurality of charging chambers by adhering a second light-transmitting base substrate to a surface of the first light-transmitting base substrate on which the sidewalls of the plurality of charging chambers are formed; and (g) cutting the first and second light-transmitting base substrates which are adhered to each other such that the plurality of charging chambers are divided into individual charging chambers.

The steps (a) to (e) of the method for manufacturing a sample storage device in accordance with the third embodiment are the same as or similar to the steps (a) to (e) of the method for manufacturing a sample storage device in accordance with the second embodiment, repeated descriptions will be omitted herein, and descriptions will be made for only the steps (f) and (g).

First, the step (f) will be described.

Figure 25:
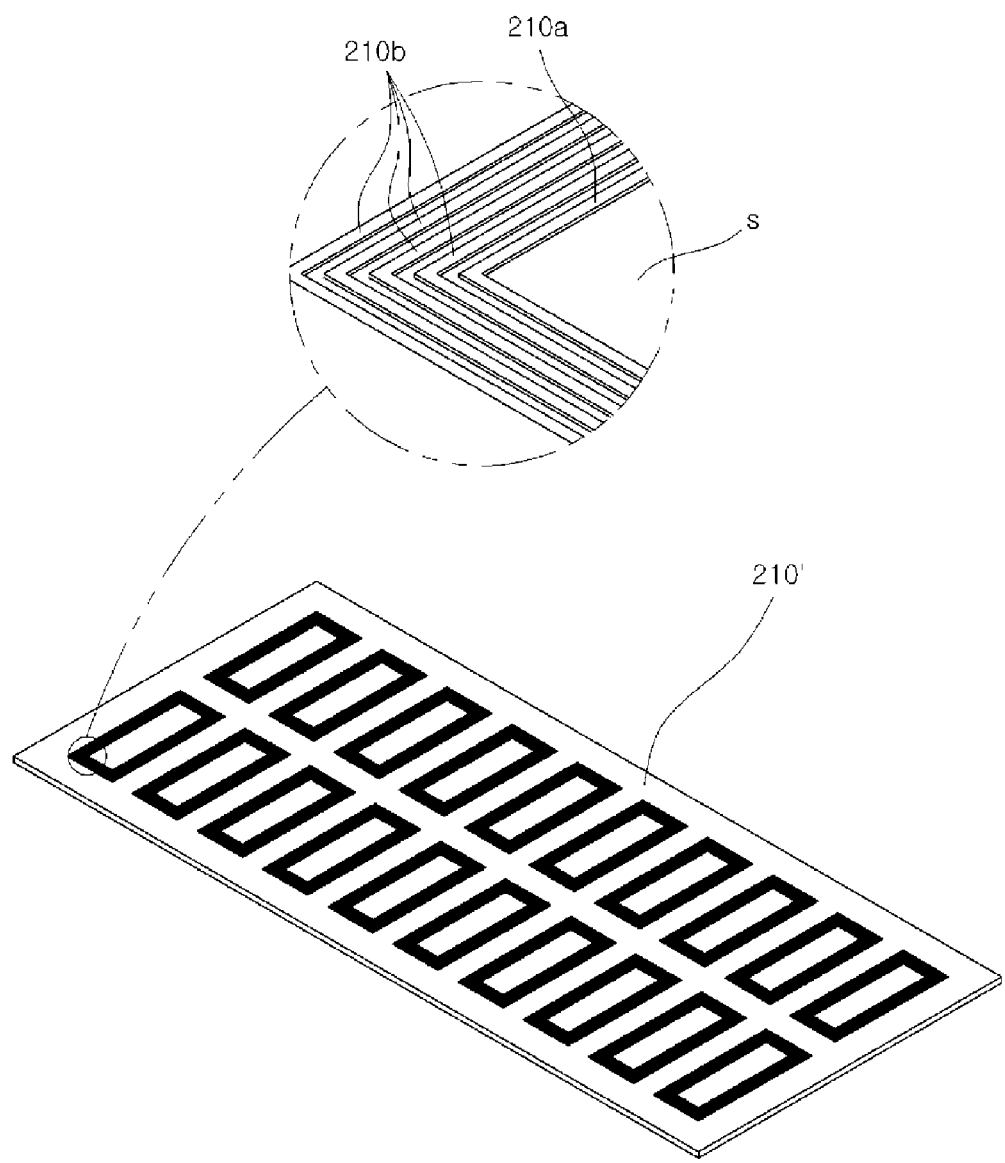
FIG. 25 is a perspective view illustrating a first light-transmitting base substrate which is formed with a plurality of charging chamber sidewalls, in accordance with a third embodiment.

The step (f) is the step of forming the plurality of charging chambers s by adhering a second light-transmitting base substrate 220' (see FIG. 26) to a surface of the first light-transmitting base substrate 210' (see FIG. 25) on which the sidewalls 210a of the plurality of charging chambers s are formed.

Figure 26:
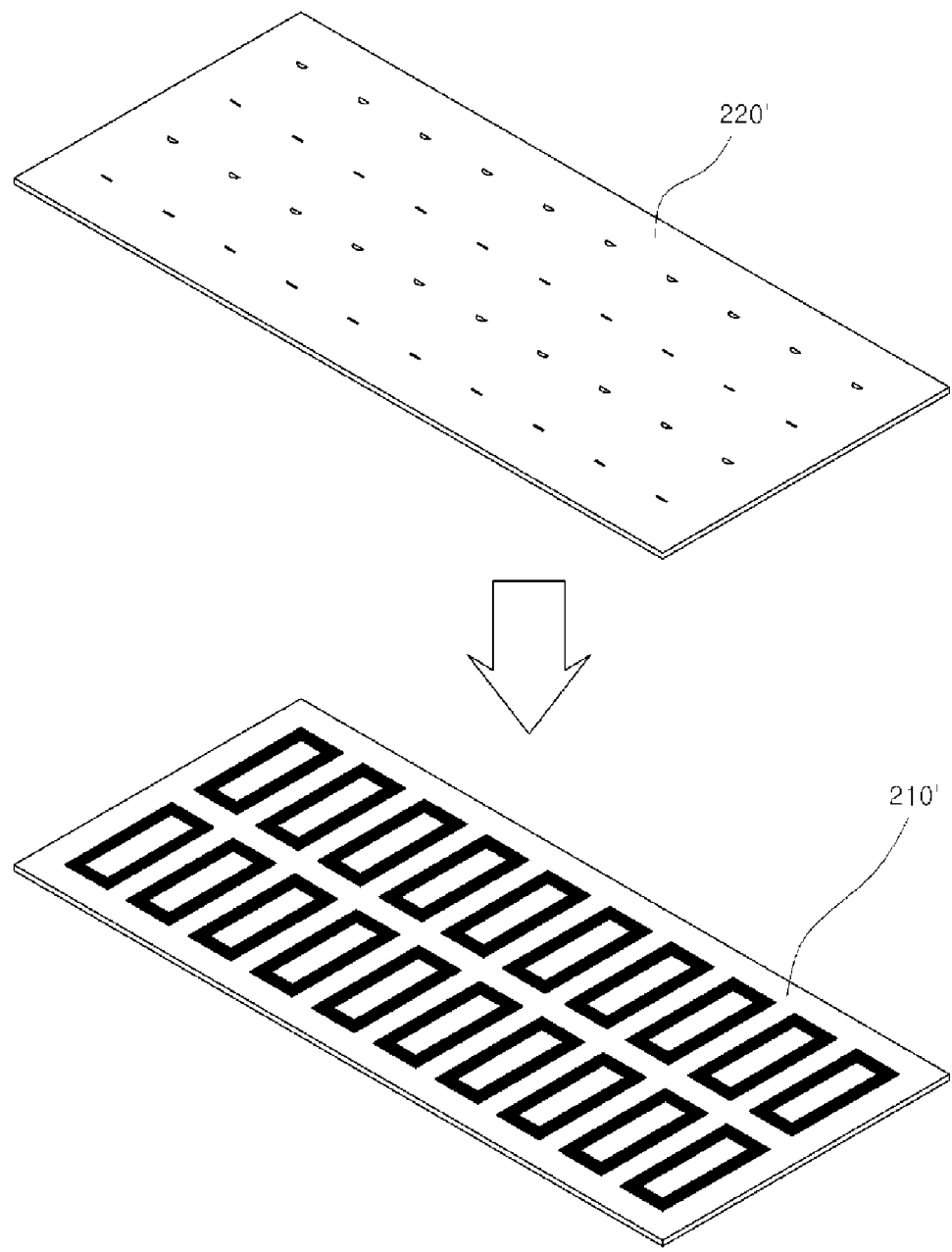
FIGS. 26 and 27 are perspective views illustrating the process of adhering the first light-transmitting base substrate formed with the plurality of charging chamber sidewalls and a second light-transmitting base substrate in accordance with the third embodiment.

As shown in FIG. 26, the second light-transmitting base substrate 220' is formed to have substantially the same area as the first light-transmitting base substrate 210', and is formed with a plurality of introducing parts 220a for charging samples into the respective charging chambers s and a plurality of discharging parts 220b for discharging the samples or air.

The first light-transmitting base substrate 210' and the second light-transmitting base substrate 220' may be adhered to each other by stacking them through applying a UV curable adhesive between them excluding regions corresponding to the charging chambers s and then radiating UV.

The step (g) will be described.

The step (g) is the step of cutting the first and second light-transmitting base substrates 210' and 220' which are adhered to each other such that the plurality of charging chambers s are divided into individual charging chambers s.

Figure 27:
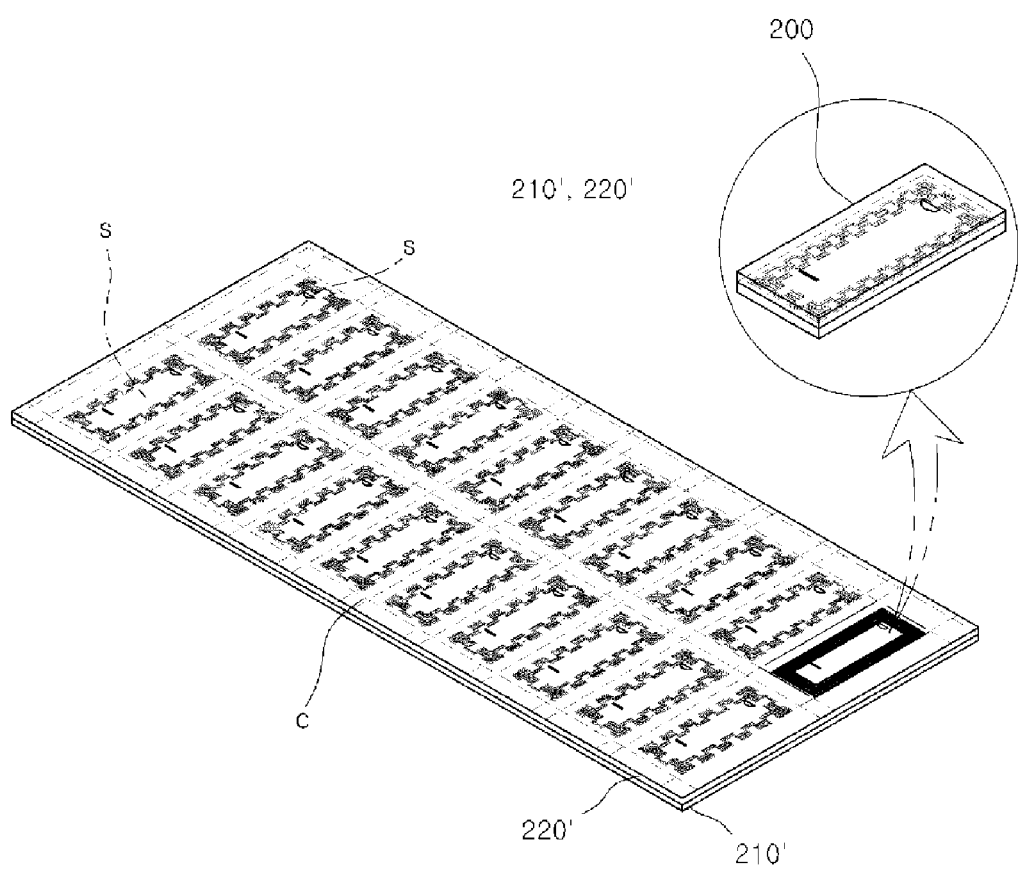

For example, as shown in FIG. 27, between the first light-transmitting base substrate 210' and the second light-transmitting base substrate 220' which are formed through the above steps (a) to (f) and are adhered to each other, the sidewalls 210a and the line walls 210b which form the individual charging chambers s are arranged in the form of 2×10.

Therefore, by cutting the first light-transmitting base substrate 210' and the second light-transmitting base substrate 220' which are adhered to each other, along imaginary cutting lines c, a single sample storage device may be completed as in the sample storage device according to the first embodiment shown in FIG. 15.

The pattern forming mold used in the method for manufacturing a sample storage device according to the embodiments uses a plate-shaped mold as described above.

Figure 28:
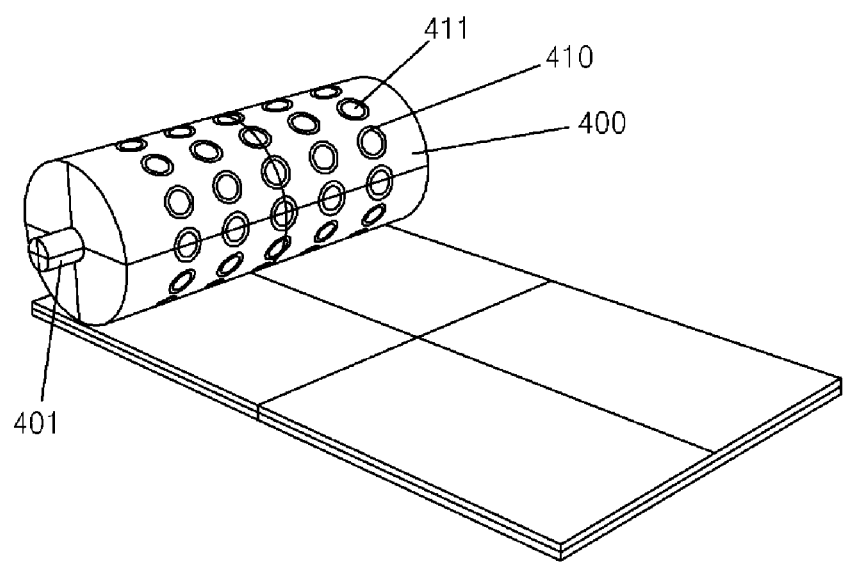
FIG. 28 is a perspective view illustrating an example of a roll type pattern forming mold in accordance with an embodiment.

FIG. 28 is a perspective view illustrating an example of a roll type pattern forming mold in accordance with an embodiment.

Referring to FIG. 28, a pattern forming mold 400 to be used in a method for manufacturing a sample storage device according to an embodiment may be used as a roll type.

The roll type pattern forming mold 400 has shafts 401 which are connected with a rotation shaft of a rotator (not shown) such as a motor, on both ends thereof, and is formed to have a circular sectional shape. Engraved pattern parts 410 are formed on the circumferential outer surface of the pattern forming mold 400 at positions with regular intervals. Protuberances 411 for forming charging chambers are formed in spaces inside the respective engraved pattern parts 410.

Therefore, in the embodiment, as the roll type pattern forming mold 400 is used, substrates may be continuously manufactured, and thus, the manufacturing speed and the yield may be increased.

A sample storage device provided in accordance with an embodiment is manufactured through the above-described methods.

While various embodiments have been described above, it will be understood to those skilled in the art that the embodiments described are by way of example only. Accordingly, the disclosure described herein should not be limited based on the described embodiments.

The invention claimed is:

1. A method for manufacturing a sample storage device having at least one charging chamber to count fine particles contained in a sample charged in the charging chamber, the method comprising:
   preparing a pattern forming mold which has an engraved pattern part for forming at least a sidewall of the charging chamber, on an upper surface thereof, wherein the engraved pattern comprises a grid pattern, wherein the engraved pattern part include a sidewall pattern for forming the sidewall of the charging chamber, and a plurality of line patterns spaced apart from one another by a predetermined interval at a region outside the sidewall pattern;
   pouring a predetermined amount of a liquid UV curable resin to be accommodated in the engraved pattern part, on the upper surface of the pattern forming mold;
   seating a first light-transmitting substrate on the upper surface of the pattern forming mold and pressing them to each other;
   radiating UV with the liquid UV curable resin accommodated in the engraved pattern part and thereby curing the liquid UV curable resin;
   separating the first light-transmitting substrate which has the sidewall of the charging chamber formed as the liquid UV curable resin is cured, from the pattern forming mold; and
   forming the charging chamber by adhering a second light-transmitting substrate to a surface of the first light-transmitting substrate on which the sidewall is formed,
   wherein the second light-transmitting substrate has an introducing part and an discharging part, the introducing part is configured to receive the sample comprising the fine particles into the charging chamber, the discharging part is configured to permit the sample or air in the charging chamber to leave the charging chamber, and the introducing part and the discharging part span an entirety of a thickness of the second light-transmitting substrate, and
   wherein the first light-transmitting substrate comprises a grid scale corresponding to the grid pattern of the forming mold.

2. A method for manufacturing a sample storage device having at least one charging chamber to count fine particles contained in a sample charged in the charging chamber, the method comprising:
   preparing a pattern forming mold which has an engraved pattern part for forming at least a sidewall of the charging chamber, on an upper surface thereof, the engraved pattern part being formed such that a plurality of pattern parts each of which forms a sidewall of a single charging chamber are arranged therein and thereby form sidewalls of a plurality of charging chambers, wherein the engraved pattern comprises at least one grid pattern, wherein the engraved pattern part include a sidewall pattern for forming the sidewall of the charging chamber, and a plurality of line patterns spaced apart from one another by a predetermined interval at a region outside the sidewall pattern;
   pouring a predetermined amount of a liquid UV curable resin to be accommodated in the engraved pattern part, on the upper surface of the pattern forming mold;
   seating a first light-transmitting base substrate on the upper surface of the pattern forming mold and pressing them to each other;
   radiating UV with the liquid UV curable resin accommodated in the engraved pattern part and thereby curing the liquid UV curable resin;
   separating the first light-transmitting base substrate which has the sidewalls of the plurality of charging chambers formed as the liquid UV curable resin is cured, from the pattern forming mold;
   cutting the first light-transmitting base substrate such that the sidewalls of the plurality of charging chambers are divided into individual sidewalls of individual charging chambers and thereby defining first light-transmitting substrates; and
   forming each charging chamber by adhering a second light-transmitting substrate to a surface of each first light-transmitting substrate on which the sidewall is formed,
   wherein the second light-transmitting substrate has an introducing part and an discharging part, the introducing part is configured to receive the sample comprising the fine particles into the charging chamber, the discharging part is configured to permit the sample or air in the charging chamber to leave the charging chamber, and the introducing part and the discharging part span an entirety of a thickness of the second light-transmitting substrate, and
   wherein the first light-transmitting substrate comprises at least one grid scale corresponding to the at least one grid pattern of the forming mold.

* * * * *